(12) United States Patent
Sowers

(10) Patent No.: US 10,400,255 B2
(45) Date of Patent: Sep. 3, 2019

(54) METHOD OF CONVERTING MARINE FISH WASTE TO BIOMETHANE

(71) Applicant: University of Maryland Baltimore County, Baltimore, MD (US)

(72) Inventor: Kevin R. Sowers, Ellicott City, MD (US)

(73) Assignee: UNIVERSITY OF MARYLAND BALTIMORE COUNTY, Baltimore, MD (US)

(*) Notice: Subject to any disclaimer, the term of this patent is extended or adjusted under 35 U.S.C. 154(b) by 19 days.

(21) Appl. No.: 15/378,480

(22) Filed: Dec. 14, 2016

(65) Prior Publication Data
US 2017/0166929 A1 Jun. 15, 2017

Related U.S. Application Data

(60) Provisional application No. 62/266,882, filed on Dec. 14, 2015.

(51) Int. Cl.
| | | |
|---|---|---|
| C12P 5/02 | (2006.01) | |
| C12P 1/04 | (2006.01) | |
| C12N 1/20 | (2006.01) | |
| C12P 39/00 | (2006.01) | |

(52) U.S. Cl.
CPC .............. *C12P 5/023* (2013.01); *C12N 1/20* (2013.01); *C12P 39/00* (2013.01); *Y02E 50/343* (2013.01)

(58) Field of Classification Search
None
See application file for complete search history.

(56) References Cited

U.S. PATENT DOCUMENTS

| | | |
|---|---|---|
| 6,443,097 B1 | 9/2002 | Zohar et al. |
| 8,997,694 B2 | 4/2015 | Sowers et al. |
| 2011/0039321 A1 | 2/2011 | Tal et al. |

FOREIGN PATENT DOCUMENTS

| | | |
|---|---|---|
| WO | 03032718 A2 | 4/2003 |
| WO | 2008131403 A1 | 10/2008 |

OTHER PUBLICATIONS

Apolinario, E., et al., "Plate colonization of Methanococcus maripaludis and Methanosarcina thermophila in a modified canning jar", "FEMS Microbiology Letters", 1996, pp. 131-137, vol. 145.
Aspe, E., et al., "Anaerobic Treatment of Fishery Wastewater Using a Marine Sediment Inoculum", "Water Research", 1997, pp. 2147-2160, vol. 31, No. 9.
Berkaw, M., et al., "Anaerobic ortho Dechlorination of Polychlorinated Biphenyls by Estuarine Sediments from Baltimore Harbor", "Applied and Environmental Microbiology", Jul. 1996, pp. 2534-2539, vol. 62, No. 7.
Bhattacharya, S. K., et al., "Interaction Between Acetate Fed Sulfate Reducers and Methanogens", "Water Research", 1996, pp. 2239-2246, vol. 30, No. 10.
Bitton, G., "Wastewater Microbiology", 2005, pp. 347-369, Published in: New York.
Cahill, M. M., "Bacterial Flora of Fishes a Review", "Microbial Ecology", Jan. 1990, pp. 21-41, vol. 19, No. 1.
Chen, Y., et al., "Inhibition of anaerobic digestion process A review", "Bioresource Technology", 2008, pp. 4044-4064, vol. 99.
Coenye, T., et al., "Intragenomic heterogeneity between multiple 16S ribosomal RNA operons in sequenced bacterial genomes", "FEMS Microbiology Letters", Nov. 3, 2003, pp. 45-49, vol. 228.
Demirel, B., et al., "Trace element requirements of agricultural biogas digesters during biological conversion of renewable biomass to methane", "Biomass and Bioenergy", Jan. 3, 2011, pp. 992-998, vol. 35.
D'Orbcastel, E. R., et al., "The wastes from marine fish production systems: characterization, minimization, treatment and valorization", "World Aquaculture Society Magazine", Sep. 2006, p. 28, 30-35, 70.
Flaherty, M., et al., "Low Salinity Inland Shrimp Farming in Thailand", "AMBIO: A Journal of the Human Environment", May 2000, pp. 174-179, vol. 29, No. 3.
Gebauer, R., "Mesophilic anaerobic treatment of sludge from saline fish farm effluents with biogas production", "Bioresource Technology", 2004, pp. 155-167, vol. 93.
Guerrero, L., et al., "Treatment of Saline Wastewaters from Fish Meal Factories in an Anaerobic Filter under Extreme Ammonia Concentrations", "Bioresource Technology", Mar. 12, 1997, pp. 69-78, vol. 61.
Jarrell, K.F., et al., "Nutritional requirements of the methanogenic archaebacteria", "Canadian Journal of Microbiology", 1988, pp. 557-576, vol. 34.
Jeison, D., et al., "Impact of high saline wastewaters on anaerobic granular sludge functionalities", "Water Science and Technology", 2008, pp. 815-819, vol. 57, No. 6.
Kabiri, L., et al., "Assessment of Human Microbial Pollution of Surface Waters by Microbial Source Tracking", "Water and Environmental Technology Center", Dec. 2010, pp. 1-11.

(Continued)

*Primary Examiner* — Yong D Pak
(74) *Attorney, Agent, or Firm* — Hultquist, PLLC; Steven J. Hultquist

(57) ABSTRACT

Methods employed for the discovery, enrichment, and characterization of a marine consortium of fermentative and methanogenic microorganisms developed from the solid waste digestor of a fully contained, land-based, marine recirculating aquaculture system are described. The methanogenic microbial consortium discovered is capable of reducing over 90% of marine fish waste in an aquaculture system to biomethane and carbon dioxide at saline concentrations found in marine aquaculture. Systems and methods for the treatment of marine fish waste utilizing the methanogenic marine consortium are also disclosed.

20 Claims, 9 Drawing Sheets
Specification includes a Sequence Listing.

(56) References Cited

OTHER PUBLICATIONS

Kjellerup, B., et al., "Site-specific microbial communities in three PCB-impacted sediments are associated with different in situ dechlorinating activities", "Environmental Microbiology", Feb. 24, 2008, pp. 1296-1309, vol. 10, No. 5.

Lane, D.J., et al., "Rapid determination of 16S ribosomal RNA sequences for phylogenetic analyses", "Proceedings of the National Academy of Sciences", Oct. 1985, pp. 6955-6959, vol. 82.

Lupatsch, I., et al., "Predicting aquaculture waste from gilthead seabream (*Sparus aurata*) culture using a nutritional approach", "Aquatic Living Resources", Aug. 27, 1998, pp. 265-268, vol. 11, No. 4.

Mirzoyan, N., et al., "Quality of brackish aquaculture sludge and its suitability for anaerobic digestion and methane production in an upflow anaerobic sludge blanket (UASB) reactor", "Aquaculture", Apr. 7, 2008, pp. 35-41, vol. 279.

Moody, L., et al., "Use of Biochemical Methane Potential (BMP) Assays for Predicting and Enhancing Anaerobic Digester Performance", "44th Croatian & 4th International Symposium on Agriculture", 2009, pp. 930-934.

Mshandete, A., et al., "Anaerobic batch co-digestion of sisal pulp and fish wastes", "Bioresource Technology", Mar. 6, 2004, pp. 19-24, vol. 95.

Muyzer, G., et al., "Profiling of Complex Microbial Populations by Denaturing Gradient Gel Electrophoresis Analysis of Polymerase Chain Reaction-Amplified Genes Coding for 16S rRNA", "Applied and Environmental Microbiology", Mar. 1993, pp. 695-700, vol. 59, No. 3.

Naylor, R.L., et al., "Nature's Subsidies to Shrimp and Salmon Farming", "Science", Oct. 30, 1998, pp. 883-884, vol. 282, No. 5390.

Omil, F., et al., "Characterization of Biomass from a Pilot Plant Digester Treating Saline Wastewater", "J. Chem. Tech. BiotechnoL", 1995, pp. 384-392, vol. 63.

Omil, F., et al., "Anaerobic treatment of seafood processing waste waters in an industrial anaerobic pilot plant", "Water SA", Apr. 1996, pp. 173-181, vol. 22, No. 2.

Payne, R.B., et al., "Enhanced Reductive Dechlorination of Polychlorinated Biphenyl Impacted Sediment by Bioaugmentation with a Dehalorespiring Bacterium", "Environmental Science & Technology", Sep. 8, 2011, pp. 8772-8779, vol. 45.

Quinn, B.M., et al., "Characterization of a microbial consortium that converts mariculture fish waste to biomethane", "Aquaculture", Dec. 2, 2015, pp. 154-162, vol. 453.

Sowers, K.R., et al., "Characterization of a Marine Methanogenic Consortium", "International Gas Research Conference. Government Institutes, Inc.", 1984, pp. 527-236.

Sowers, K.R., et al., "Disaggregation of *Methanosarcina* spp. and Growth as Single Cells at Elevated Osmolarity", "Applied and Environmental Microbiology", Nov. 1993, pp. 3832-3839, vol. 59, No. 11.

Sowers, K.R., et al., "A Laboratory Manual; Techniques for Anaerobic Growth", 1995, pp. 15-47.

Sowers, K.R., et al., "Methanogenesis in the Marine Environment", "The Encyclopedia of Environmental Microbiology", 2002, pp. 1913-1923, Publisher: John Wiley & Sons, Inc.

Sowers, K.R., "Methanogenesis", "Encyclopedia of Microbiology, 3rd Edition", 2009, pp. 265-286, Edited by: Schaechter, M., Publisher: Elsevier, Academic Press.

Sowers, K. R., "Methanogenesis Chapter 11", "Metabolism and Behavior of Diverse Microbes", 2011, pp. 1-28.

Sowers, K. R., "Methanogenesis", "Reference Module in Biomedical Research", 2015, pp. 1-21.

Staley, J.T., et al., "Phylum XIX. Fusobacteria", "Bergey's Manual of Systematic Bacteriology", 2011, pp. 747-765.

Surkov, A.V., et al., "*Dethiosulfovibrio russensis* sp. nov., *Dethiosulfovibrio marinus* sp. nov. and *Dethiosulfovibrio acidaminovorans* sp. nov., novel anaerobic, thiosulfate- and sulfur-reducing bacteria isolated from Thiodendron sulfur mats in different saline environments", "International Journal of Systematic and Evolutionary Microbiology", 2001, pp. 327-337, vol. 51.

Tal, Y., et al., "Environmentally sustainable land-based marine aquaculture", "Aquaculture", Jan. 7, 2009, pp. 28-35, vol. 286.

Wagner, A.O., et al., "Application of Denaturing High-Performance Liquid Chromatography in Microbial Ecology: Fermentor Sludge, Compost, and Soil Community Profiling", "Applied and Environmental Microbiology", Feb. 2009, pp. 956-964, vol. 75, No. 4.

Wolin, E.A., et al., "Formation of Methane by Bacterial Extracts", "The Journal of Biological Chemistry", Aug. 1963, pp. 2882-2886, vol. 238, No. 8.

Wu, G.D., et al., "Linking Long-Term Dietary Patterns with Gut Microbial Enterotypes", "Science", Oct. 7, 2011, pp. 105-108, vol. 334.

Zhang, X., et al., "Potentials and limitations of biomethane and phosphorus recovery from sludges of brackish/marine aquaculture recirculation systems: A review", "Journal of Environmental Management", Sep. 22, 2013, pp. 44-54, vol. 131.

Zhao, J.-S., et al., "*Psychrilyobacter atlanticus* gen. nov., sp. nov., a marine member of the phylum Fusobacteria that produces H2 and degrades nitramine explosives under low temperature conditions", "International Journal of Systemic and Evolutionary Microbiology", 2009, pp. 491-491, vol. 59.

NOTE: For the non-patent literature citations that no month of publication is indicated, the year of publication is more than 1 year prior to the effective filing date of the present application.

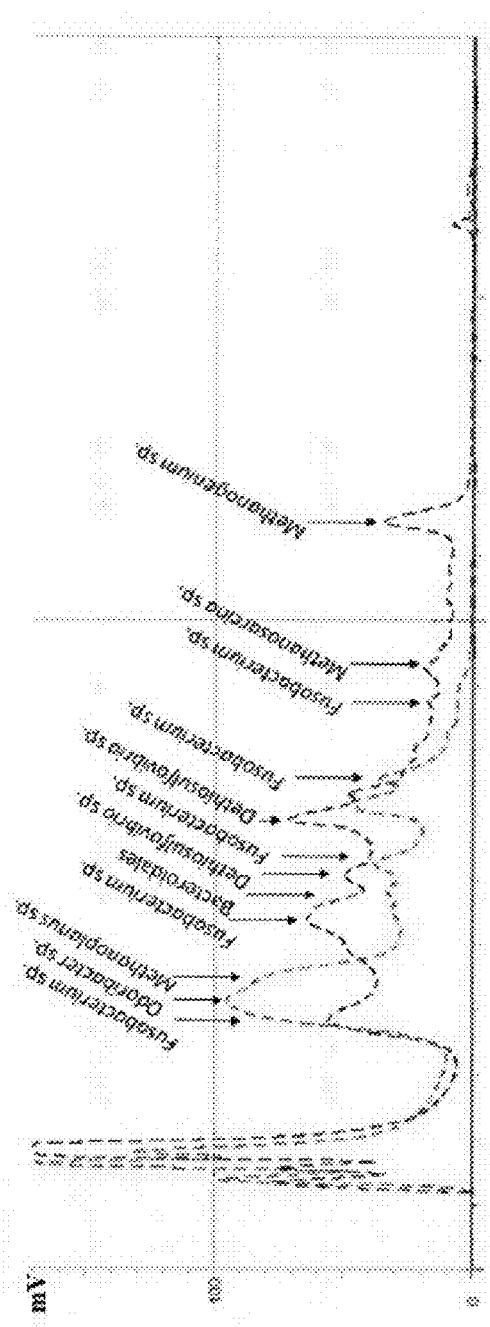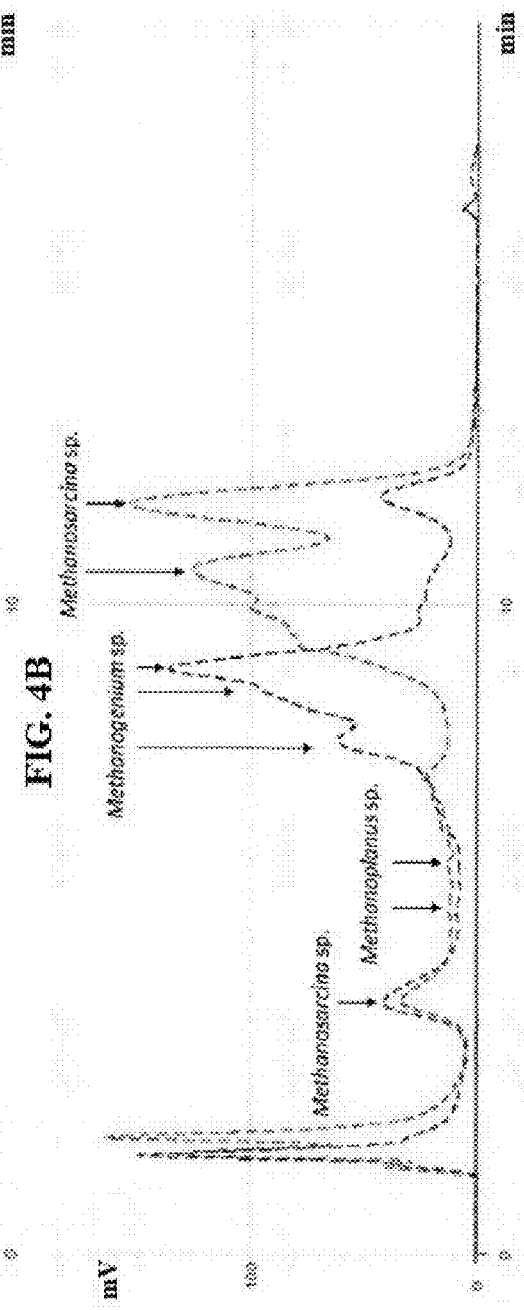

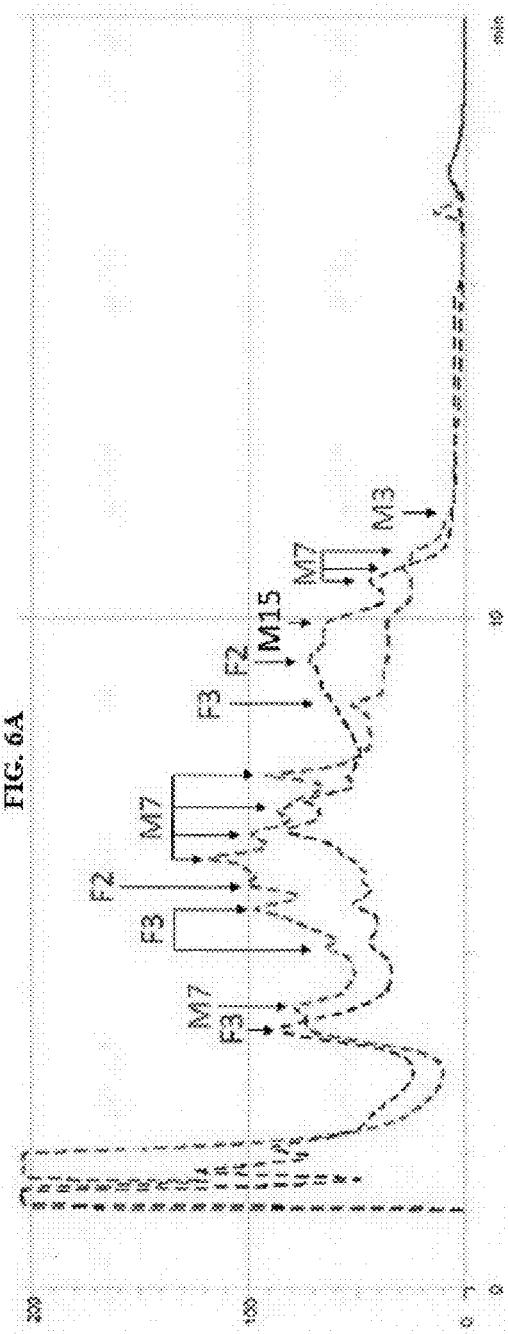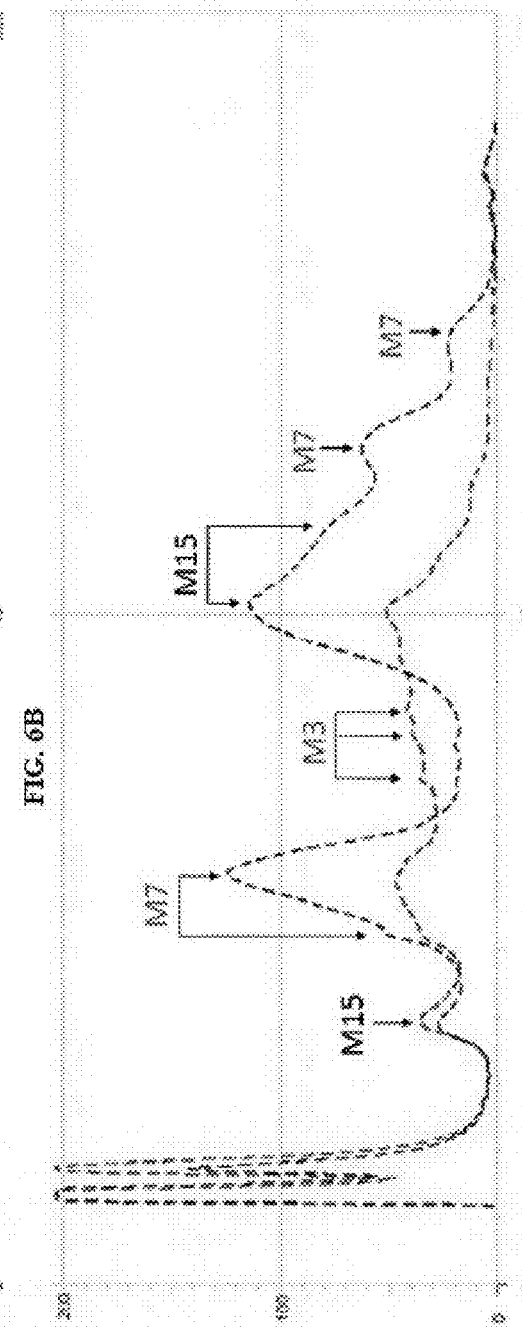

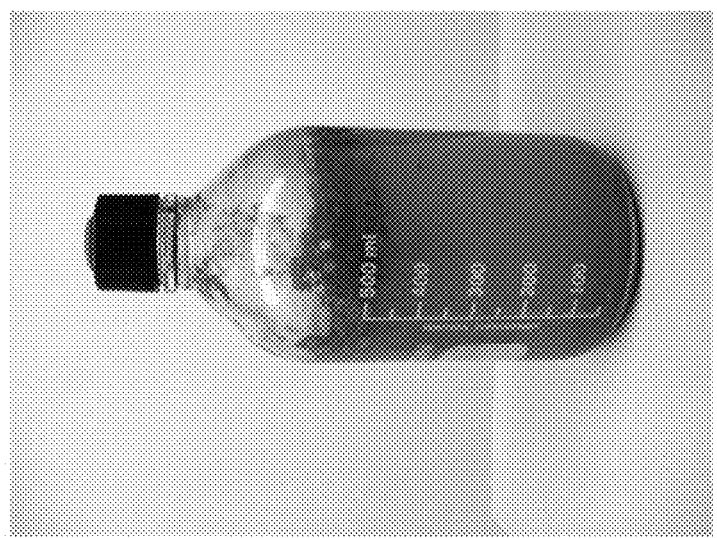
FIG. 9

METHOD OF CONVERTING MARINE FISH WASTE TO BIOMETHANE

CROSS REFERENCE TO RELATED APPLICATION

This application claims the benefit under 35 U.S.C. § 119 of U.S. Provisional Patent Application No. 62/266,882 filed Dec. 14, 2015. The disclosure of U.S. Provisional Patent Application No. 62/266,882 is hereby incorporated herein by reference in its respective entirety, for all purposes.

GOVERNMENT RIGHTS IN THE INVENTION

This invention was made with government support under Research Grant Award No. US-4453-11 from the United States-Israel Binational Agricultural Research and Development Fund (BARD). The government has certain rights in the invention.

FIELD

The present disclosure relates to a methanogenic microbial consortium and systems and methods for use thereof in conversion of organic waste, such as marine fish waste, to biomethane.

DESCRIPTION OF THE RELATED ART

Marine fisheries have been in continuous decline globally and projections indicate that a collapse in the industry is imminent within a few decades if current levels of trade continue. In order to ease pressures on wild fisheries stocks, and to meet the growing global consumption of seafood, there is a growing reliance on aquaculture of marine species. One of the major drawbacks of marine aquaculture is localized eutrophication due to release of waste products. The potential adverse effects of net-pen mariculture on the environment have been widely publicized and the issue has become a source of controversy between environmentalists and marine fish farmers.

Appropriate disposal of solid organic wastes from land-based brackish and marine recirculating aquaculture systems is critical for promoting widespread acceptance and implementation, but conversion efficiency of saline waste or sludge to biomethane is generally low.

In response to the growing demand for farmed seafood products, intensive Recirculating Aquaculture Systems (RAS) are being developed as an eco-responsible alternative to traditional aquaculture technologies. However, there has been negligible research on decreasing the environmental impact of saline organic waste generated by RAS.

A future shift from net-pen mariculture operations to more inland recirculating aquaculture systems will result in the generation of high volumes of saline waste/sludge. The output from intensive RAS is primarily composed of suspended matter originating from uneaten feed and fish fecal material. Significant portions of the fish feed (25-50%) typically end up as organic waste. An aquaculture facility with a standing fish crop of 100 tons and a daily feeding rate of 2% of fish body weight will produce annually 12-43 tons of dry organic waste as total suspended solids (TSS). The actual volume of the collected waste after settling is 10 times higher and can reach a volume of 2200-2900 m³. It has been calculated (Hardy, 2000, Aquaculture Magazine 26(6):47-50) that a 100 ton salmon farm releases an amount of nitrogen, phosphorus and fecal matter roughly equivalent to the nutrient waste in untreated sewage from 20,000, 25,000 and 65,000 people, respectively. Most commonly used sludge treatments employ flocculation/coagulation processes to reduce sludge volume prior to composting it for land dispersal. However, unlike sludge or waste from freshwater RAS, the high salinity of brackish/marine sludge or waste limits its use as fertilizer and creates a source of pollution in landfill sites and waste outflows (Flaherty et al., 2000, AMBIO: A Journal of the Human Environment 29, 174-179; Naylor et al., 1998, Science 282, 883-884).

One solution for treating saline organic waste from an intensive marine RAS, a closed-loop system, and achieve near-zero discharge, is to reduce the organic waste volume by converting it to biomethane and carbon dioxide gases in an anaerobic digestor. Bioreactors containing methanogenic consortia of bacteria and archaea can digest high organic loads at low operating costs and with relatively low initial investment. Furthermore, the end product of anaerobic biomass conversion, biomethane, can offset some of the operational costs as a combustible energy source for heat or generation of electricity. Since the carbon dioxide generated from both biomass reduction and biomethane combustion is from an organic non-petroleum source, there is no net release of greenhouse gas into the atmosphere. Partial substitution of biomethane for petroleum-based fuels to power or heat the RAS would effectively reduce the carbon footprint of the system.

However, several characteristics of concentrated fish waste from recirculating mariculture systems can adversely affect biomass conversion by methanogenic consortia, including: 1) high NaCl concentrations associated with seawater requiring microorganisms adapted to growth in high extracellular solute concentrations; 2) accumulation of toxic levels of sulfide from the reduction of the high sulfate levels in seawater by sulfate reducing bacteria; and 3) accumulation of ammonia from catabolism of highly proteinaceous fish feed by fish and fermentative bacteria.

Prior studies on anaerobic digestion of marine fish waste using inoculum from non-marine sources such as municipal or industrial sludge digestors or pig manure were subject to long adaptation periods and results were mixed (Gebauer, 2004, Bioresource technology 93, 155-167; Omil et al., 1996, Water SA 22, 1 73-181; Omil et al., 1995, J. Chem. Technol. Biotechnol. 63, 384-392). In contrast, Aspe et al (Aspe et al., 1997, Water research 31, 2147-2160) reported that inoculum from marine sediments developed more rapidly and was more effective at treating marine fish wastewater than inoculum from pig manure. These results are consistent with a report by Sowers and Ferry (Sowers et al., 1984, Characterization of a Marine Methanogenic Consortium, International Gas Research Conference. Government Institutes, Inc., Washington, D.C., pp. 316-325), which described the development of a stable consortium of marine fermenters, acetogens and methanogens enriched from marine sediments with marine kelp (*Macrocyctis pyrifera*) that converted over 90% of the biomass to methane and carbon dioxide in seawater. Isolates in the consortium had equivalent roles to those in freshwater methanogenic consortia, but were uniquely adapted to growth and biogas production from algal carbohydrates at marine saline levels. In contrast, marine fish waste is highly proteinaceous requiring consortia that can convert organic nitrogen in the form of proteins and amino acids to biomethane.

Several reports describe the microbiota involved in aerobic and anaerobic nitrogen processing but insights into the population dynamics of microbiota in the biogas reactors of a marine RAS have not been reported.

Thus, there remains a need in the art for a stable marine microbial consortium capable of reducing fish waste biomass to methane and carbon dioxide at high saline concentrations and systems for use thereof in the treatment of fish waste from marine aquaculture systems.

SUMMARY

The present disclosure describes methods employed for the discovery, enrichment, and characterization of a marine consortium of fermentative and methanogenic microorganisms developed from the solid waste digestor of a fully contained, land-based, marine recirculating aquaculture system. The methanogenic microbial consortium discovered is capable of reducing over 90% of fish waste in the aquaculture system to methane and carbon dioxide at saline concentrations found in marine aquaculture. The disclosure also relates to systems and methods for the treatment of fish waste utilizing such methanogenic marine consortium.

In one aspect, the disclosure relates to a methanogenic microbial consortium for conversion of marine fish waste to biomethane comprising two isolates of anaerobic fermentative bacteria and three isolates of archaea. The methanogenic microbial consortium may provide the complete methanogenic microbial consortium used in a bioreactor for conversion of marine fish waste to biomethane. In embodiments, the methanogenic microbial consortium for conversion of marine fish waste to biomethane comprises (a) an isolated *Dethiosulfovibrio* sp. microorganism comprising the 16S ribosomal subunit nucleotide sequence of SEQ ID NO: 1;

(b) an isolated *Fusobacteriacea* microorganism comprising the 16S ribosomal subunit nucleotide sequence of SEQ ID NO: 2;

(c) an isolated *Methanogenium* sp. microorganism comprising the 16S ribosomal subunit nucleotide sequence of SEQ ID NO: 3;

(d) an isolated *Methanoplanus* sp. microorganism comprising the 16S ribosomal subunit nucleotide sequence of SEQ ID NO: 4;

(e) an isolated *Methanosarcina* sp. microorganism comprising the 16S ribosomal subunit nucleotide sequence of SEQ ID NO: 5.

In another aspect, the disclosure relates to a method for conversion of marine fish waste to biomethane, comprising exposing the marine fish waste to a methanogenic microbial consortium comprising two isolates of anaerobic fermentative bacteria and three isolates of archaea. In such aspects, the methanogenic microbial consortium may comprise (a) an isolated *Dethiosulfovibrio* sp. microorganism comprising the 16S ribosomal subunit nucleotide sequence of SEQ ID NO: 1;

(b) an isolated *Fusobacteriacea* microorganism comprising the 16S ribosomal subunit nucleotide sequence of SEQ ID NO: 2;

(c) an isolated *Methanogenium* sp. microorganism comprising the 16S ribosomal subunit nucleotide sequence of SEQ ID NO: 3;

(d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5. The conversion of marine fish waste to biomethane takes place under anaerobic conditions effective for microbial action on the marine fish waste to produce biomethane.

In another aspect, the disclosure relates to a closed, recirculating marine aquaculture system comprising brackish or salt water comprising marine fish waste, a tank comprising a marine species, and a methanogenic bioreactor comprising a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5.

In a further aspect, the disclosure relates to a biomethane production apparatus, comprising a bioreactor containing a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5.

In a still further aspect, the disclosure relates to a method of producing biomethane, the method comprising exposing a methanogenic substrate to a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5 under conditions effective to microbially generate biomethane, and separating the generated biomethane from the microbial consortium to recover a biomethane product.

Other aspects, features and embodiments of the invention will be more fully apparent from the ensuing disclosure and appended claims.

BRIEF DESCRIPTION OF THE DRAWINGS

FIGS. 4A and 4B are denaturing HPLC chromatograms of phylotypes detected after initial enrichment (gray) and after seven transfers (black). FIG. 4A shows phylotypes detected with primers specific for the gene encoding methyl coenzyme M reductase in methanogenic Archaea. FIG. 4B shows phylotypes detected with primers specific for the gene encoding 16S rRNA in Bacteria and Archaea. Unlabeled peaks did not yield a sequence.

FIGS. 6A and 6B are denaturing HPLC chromatograms of phylotypes detected in medium with sterile fish waste inoculated with enrichment consortium (gray) and the reconstituted consortium (black). FIG. 6A shows phylotypes detected with primers specific for the gene encoding 16S rRNA in bacteria and archaea. FIG. 6B shows phylotypes detected with primers specific for the gene encoding methyl coenzyme M reductase (mcrA) in methanogenic archaea. Strain designations are as follows: *Fusobacteriacea* EA-F3 (F3), *Dethiosulfovibrio* sp. EA-F2 (F2), *Methanogenium* sp. EA-M3 (M3), *Methanoplanus* sp. EA-M7 (M7), *Methanosarcina* sp. EA-M 15 (M I 5). Unlabeled peaks did not yield a sequence.

FIG. 9 shows that prior to digestion the sludge (fish waste) was nearly black in color and had a thick consistency with particles remaining suspended in liquid while after digestion the sludge was light brown in color with a sandy consistency that settled out of the liquid phase.

DETAILED DESCRIPTION

Figure 1:
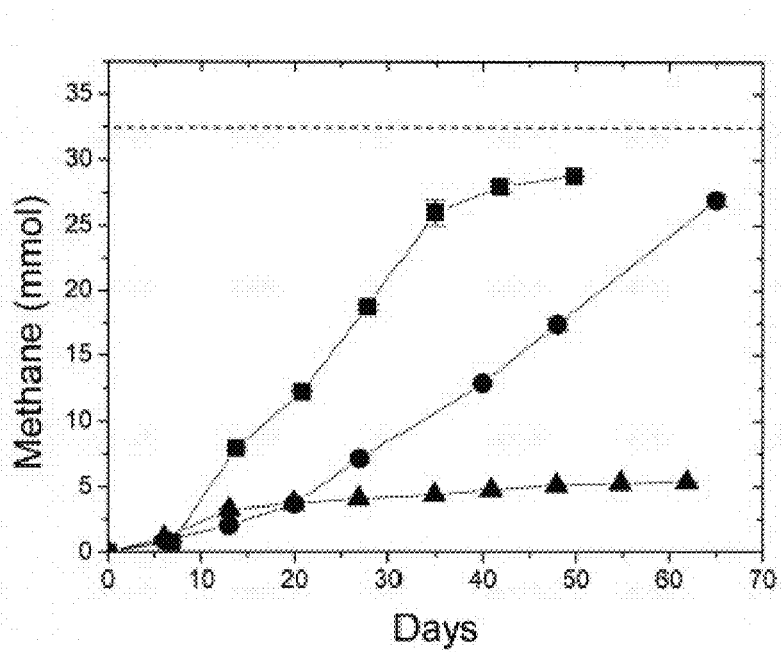
FIG. 1 is a graphical representation of the effect of sequential transfers of fish sludge enrichment on rates of methane production. The graph shows methane production for the initial (▲), third transfer (●) and seventh transfer (■) of the enrichment culture. The dashed line represents estimated maximum methane yield from total COD of sludge. Values are means and standard deviations for three replicate culture samples.

The disclosure relates to development of a methanogenic microbial consortium that is capable of converting marine fish waste to biomethane at greater than 90% efficiency. The halotolerant consortium discovered, which was developed by sequential transfer in seawater with fish waste, is optimized for low COD:N ratios typical of fish waste and does not require addition of amendments such as organic carbon or nutrients.

Five predominant phylotypes identified in the microbial consortium by denaturing HPLC were isolated. Two species were anaerobic fermenters closely related to anaerobic fermentative *Fusobacterium* spp. and *Dethiosulfovibrio* spp., which both hydrolyze and ferment proteins, peptides and amino acids. The other three isolates were anaerobic archaea and included an acetate-utilizing methanogenic archaeon closely related to *Methanosarcina* spp. and two hydrogen-utilizing methanogenic archaea closely related to *Methanogenium* spp. and *Methanoplanus* spp. The five new strains isolated and identified herein may be used to constitute a methanogenic microbial consortium beneficial for conversion of marine fish waste to biomethane.

In tests detailed in the examples, bioconversion rates of sterile fish waste with the reconstituted consortium containing all five isolates were equivalent to rates observed with the original enriched consortium after one sequential transfer. The results demonstrate unequivocally that halotolerant consortia of bacteria and archaea can be developed for bioconversion of saline fish waste with high efficiencies equivalent to those attained with non-saline waste systems.

Understanding the microbial community composition is critical for management of solid waste from land-based marine aquaculture systems and to maintain or restore microbiota during start up and throughout the production process. The disclosure herein of a methanogenic microbial consortium comprising new strains of bacteria and archaea effective in the conversion of marine fish waste provides advantages for operation of anaerobic bioreactors, including more efficient conversion and ability to scale up such bioreactors for greater throughput. By way of example, the use of the methanogenic microbial consortium as disclosed herein allows for the production of a large amount of cell mass in artificial medium which then may be utilized in an anaerobic bioreactor for the conversion of marine fish waste to biomethane. In addition, inoculum can be concentrated and used as needed to rapidly initiate an anaerobic digestor, effectively reducing the lag time to obtain optimal digestion rates from months to days or weeks. The concentrated inoculum may also be preserved and stored for long periods providing a means to initiate waste digestors at any time The terms "consortium," "consortia," and "microbial culture" as used herein all refer to a group of microorganisms combined so that the microorganisms work in a collaborative manner in order to obtain maximum biomethane from marine fish waste as a feedstock.

The term "marine" as used herein relates to saltwater-based systems including artificial seawater, for example. Marine saltwater-based systems include water with salinity ranging from that of brackish water to that of seawater. In certain embodiments, the salinity may be greater than 5 ppt. In other embodiments, the salinity of the water may be between about 10 and 50 ppt, between about 10 and 40 ppt, between about 10 and 30 ppt, between about 15 and 40 ppt, or between about 15 and 35 ppt. As used herein, "marine" excludes freshwater-based systems. The methanogenic microbial consortium is effective in saltwater-based systems, but not in freshwater-based systems.

Mariculture or marine aquaculture as used herein is the farming of aquatic plants and animals in saltwater-based water systems. A closed estuarine or marine recirculating aquaculture system (RAS) as used herein refers to an RAS of a saltwater-based system. As a closed system, the only addition may be replacement of water lost to evaporation and/or cleaning. Such closed RAS's are useful in fish farming.

The present disclosure relates to a method for producing biomethane by exposing a methanogenic substrate to a methanogenic microbial consortium under conditions effective to microbially generate biomethane. The methanogenic substrate may be any substrate on which the methanogenic microbial consortium is biologically active. In embodiments, the methanogenic substrate may be marine fish waste.

The disclosure further relates to a method of conversion of marine (saline-containing) fish waste generated by a marine aquaculture system to biomethane. Further, the disclosure relates to an anaerobic bioreactor for the digestion of marine fish waste from marine aquaculture systems and the production of methane gas. The present disclosure also relates to use of an anaerobic bioreactor in a recirculating marine aquaculture system. The disclosure further relates to a methanogenic microbial consortium capable of effecting conversion of marine fish waste to biomethane and a method of producing biomethane.

Operation of marine aquaculture systems results in production of fish waste. Such waste may include solid matter or liquid waste within the saltwater environment of the marine aquaculture system. The marine fish waste may be made up of any or all of the following: saline organic solids, fish feed, fish fecal matter and fish parts, including carcasses, scales, skin or viscera, among other material known to be present in marine fish waste. Fish waste in a marine aquaculture system therefore comprises organic solids that pollute the system. Since the marine aquaculture system comprises saltwater, the waste will also include salt, such that the organic solids are saline organic solids.

In general, aquacultural solid waste includes fish metabolic by-products and uneaten feed. The fish feed typically contains protein, lipids, carbohydrate and phosphorus. By way of example, an aquaculture system where fish respiration yields 52% carbon as $CO_2$, the fish intake is 15-20% nitrogen, 22% carbon and 50% phosphorus, fish secretion is ammonia and phosphorus, and the feces and uneaten feed includes organic nitrogen, organic carbon and phosphorus, 1 kg feed results in 0.25 kg solid waste (dry weight) (D'orbcaster et al., 2006, *World Aquaculture Society Magazine*, 70:28-35).

It has now been discovered that fish waste (or sludge) from marine aquaculture systems can be effectively degraded by the methanogenic microbial consortium defined herein. The marine fish waste may be degraded by the methanogenic microbial consortium of the disclosure in an anaerobic bioreactor, more particularly a methanogenic bioreactor, capable of the conversion of organic waste, including fish waste, to biomethane. Such methanogenic bioreactor may be integrated within a marine aquaculture system for degradation or digestion of the marine fish waste produced in the system. In certain embodiments, digestible marine fish waste is the fish waste degraded or reduced based on COD (chemical oxygen demand), e.g, as measured using COD. The term "anaerobic" as used herein is used to refer to the degradation of waste in the absence of oxygen.

Any anaerobic bioreactor may be used with the methanogenic microbial consortium disclosed herein. Such bioreactors include any apparatus in which biological methanogenesis may be carried out for the production of biomethane. Such bioreactors are known in the art and include, without limitation, an upflow anaerobic filter reactor (UAF), a continuously stirred tank reactor (CSTR), an upflow anaerobic sludge blanket (UASB) reactor, and a modified upflow anaerobic sludge blanket (UASB) reactor (described in U.S Patent Publication No. 2011/0039321), among others.

Marine aquaculture systems according to the disclosure will desirably include at least one anaerobic bioreactor suitable for conversion of fish waste to biomethane in which a methanogenic microbial consortium is provided. In embodiments, the methanogenic microbial consortium comprises (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5.

In general, a marine aquaculture system is a system used in the cultivation of marine organisms, e.g., fish. Such cultivation is typically performed under controlled conditions to maximize the desired output. In the case of fish farming using such a system, the desired output is optionally measured as a measure of fish weight per volume of the aquaculture medium. Particularly desirable are systems resulting in high density yield of fish. In systems providing a high density yield of fish, however, the production of fish waste is also high.

The most critical barriers to widespread commercial development of marine RASs are the cost of saline solid waste removal and their low energy efficiency. Key advantages of treating saline fish waste by anaerobic methanogenic digestion are the requirement for minimal energy input and the production of biomethane as a product, which can be used as an energy source to further offset operating costs. Although anaerobic digesters are subject to the rate limiting steps of hydrolysis and methanogenesis, they can handle relatively high organic loading rates with minimal energy input and space requirements.

The process of anaerobic digestion requires a consortium of organisms typically consisting of an interactive consortium of hydrolytic bacteria, fermentative acidogenic bacteria, hydrogen-utilizing acetogenic bacteria and methanogenic Archaea (Bitton, 2005, Wastewater Microbiology, 3d Ed., Wiley-Lizz Inc., New York, pp. 345-370). Through the methods shown in the examples, a methanogenic microbial consortium of two anaerobic fermenters and three methanogenic Archaea have been found to be capable of converting fish waste to biomethane at high rates of efficiency. In certain embodiments, the methanogenic microbial consortium may be used as a complete consortium for conversion of fish waste to biomethane.

"Complete consortium" as used herein means that the only methanogenic microorganisms in the methanogenic microbial consortium used in a bioreactor are (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated

*Methanosarcina* sp. microorganism comprising the 16S ribosomal subunit nucleotide sequence of SEQ ID NO: 5.

As shown in the examples, factors known to adversely affect the performance of methanogenic bioreactors were investigated to determine the maximum efficiency that can be achieved by methanogenic degradation of fish waste from a marine RAS using the methanogenic microbial consortium of the disclosure.

Among the fermentative strains, strain EA-F2 has 99% sequence identity to *Dethiosulfovibrio russensis*, *acidaminovorans* and *marinus*. These species were isolated from saline environments and all three species ferment proteins, peptides and amino acids to acetate, hydrogen and carbon dioxide (Surkov et al., 2001, *Int. J. Syst. Evol. Microbiol.* 51, 327-337).

Strain EA-F3 has 92 to 96% sequence identity to species within the *Fusobacteriaceae*. Although the majority of species within this phylum were isolated from humans or animals, *Ilyobacter* spp. were isolated from marine sediments (Zhao et al., 2009, *Int. J. Syst. Evol. Microbiol.* 59, 491-497). Most species ferment proteins and amino acids to butyric, propionic and acetic acids and other fermentation products.

Strain EA-M15 has 98% sequence identity to *Methanosarcina* spp. These methanogenic Archaea, which include halotolerant and obligate marine species, utilize methylated amines, methyl sulfides, acetate and sometimes hydrogen for growth and methanogenesis (Sowers, 2009, Methanogenesis, in: Schaechter, M. (Ed.), Encylopedia of Microbiology, 3$^{rd}$ Ed. Elsevier/Academic Press, pp. 265-286).

Strain EA-M3 has 99% sequence identity to *Methanogenium* spp., and strain EA-M7 has 95% sequence identity to *Methanoplanus* spp., which are hydrogen-utilizing methanogenic Archaea that include marine species (Sowers, 2009, Methanogenesis, in: Schaechter, M. (Ed.), Encyclopedia of Microbiology, 3$^{rd}$ Ed. Elsevier/Academic Press, pp. 265-286). Despite the relatively low sequence identity of the *Methanoplanus* sp., microscopic examination revealed disc-shaped cells characteristic of this genus. Denaturing HPLC analysis of 16S rRNA genes for all of the pure cultures resulted in more than one PCR fragment, an effect that was observed previously for analysis on both DGGE gels and dHPLC (Wagner et al., 2009, *Appl. Environ. Microbiol.* 75, 956-964). Possible explanations include inaccuracy of polymerase with PCR amplification or sequence variations within the template DNA (Coenye et al., 2003, *FEMS Microbiol. Lett.* 228, 45-49). Genome sequences of species for all five of the isolates have more than one 16S rRNA gene copy, which could also create multiple peaks.

The isolated strains of bacteria and archaea of the five component methanogenic microbial consortium were identified as follows: *Dethiosulfovibrio* sp. EA-F2, KT799836, SEQ ID NO: 1; *Fusobacteriacea* EA-F3, KT799837, SEQ ID NO: 2; *Methanogenium* sp. EA-M3, KT799838, SEQ ID NO: 3; *Methanoplanus* sp. EA-M7, KT799839, SEQ ID NO: 4; *Methanosarcina* sp. EA-M15, KT799849, SEQ ID NO: 5. Thus, the methanogenic microbial consortium may be characterized as comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5.

The five component methanogenic microbial consortium is stable under conditions used for growth without fish waste and for reaction in a bioreactor for conversion of marine fish waste to biomethane. As used herein, the stability of the methanogenic microbial consortium provides the ability to maintain a stable ratio of members of the consortium through sequential transfers.

Overall, the fermentative species are well adapted for converting highly proteinaceous fish feces and partially or uneaten food in fish waste to acetate and hydrogen, which are substrates for acetotrophic and hydrogenotrophic methanogenic archaea, respectively.

In bioconversion of waste in low saline waste treatment systems, fatty acid-utilizing acetogens oxidize butyrate and propionate to the methanogenic substrates acetate and hydrogen. The absence of short chain fatty acid-utilizing acetotrophs in the consortium suggests that the hydrogen-utilizing methanogens create a thermodynamic shift towards acetate production by the fermenters via inter-species hydrogen exchange (Sowers and Ferry, 2002, Marine Methanogenesis, in: Bitton, G. (Ed.), The Encyclopedia of Environmental Microbiology. John Wiley & Sons, Inc., New York, pp. 1913-1923). Without being bound by any theory, this thermodynamic shift would cause more complete conversion of the fish waste to the methanogenic intermediates acetate and hydrogen.

The disclosure herein includes a method for conversion of marine fish waste to biomethane comprising exposing the marine fish waste to a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5, under anaerobic conditions effective for microbial action on the marine fish waste to produce biomethane.

The method for conversion may take place in a methanogenic bioreactor. In certain embodiments, the methanogenic bioreactor is an upflow anaerobic sludge blanket reactor or a modified upflow anaerobic sludge blanket reactor (described in U.S Patent Publication No. 2011/0039321).

The method for conversion of marine fish waste to biomethane using the five component methanogenic microbial consortium described herein provides conversion of above about 80% of the marine fish waste. In certain embodiments, the method for conversion of marine fish waste to biomethane provides conversion of above about 90%, based on COD. In other embodiments, over time, the conversion rate may be above about 95% of the marine fish waste, based on COD.

The efficiency of the process (above about 90%) combined with detection of these five predominant species supports the conclusion that this consortium is highly adapted for direct conversion of fish waste solids to methane without the need for additional pretreatment of the marine fish waste. Such pretreatments typically include chemical or biological hydrolysis or mechanical maceration, for example. In certain embodiments, the fish waste may be allowed to settle in a settling tank for a period of time prior to digestion with a methanogenic microbial consortium, providing some level of predigestion, depending on the time allowed for settling.

It is interesting that acetate-utilizing *Methanosaeta* spp., which are generally abundant in low-saline waste treatment systems, microbial granules formed in UASB systems, and in consortia from marine kelp digestors, were not detected in the fish waste enrichments (Sowers, 2009, Methanogenesis, in: Schaechter, M. (Ed.), Encyclopedia of Microbiology, 3$^{rd}$ ed. Elsevier/Academic Press, pp. 265-286; Sowers and Ferry, 1984, Characterization of a Marine Methanogenic Consortium, International Gas Research Conference. Government Institutes, Inc., Washington, D.C., pp. 316-325). Without being bound by any theory, one explanation could be the lack of visible granule formation resulting from high sodium concentration (Jeison et al., 2008, *Water Sci. Technol.* 57, 815-819), which is critical for preventing washout of slow growing *Methanosaeta*. However, this would not prevent growth of *Methanosaeta* in batch culture. Without being bound by any theory, a more likely explanation is that acetate concentrations were high enough so that *Methanosaeta*, which have a lower $K_s$ for acetate uptake, were overgrown by faster growing *Methanosarcina* spp.

Although the reconstituted five member consortium exhibited bioconversion rates that were equivalent to the enriched consortium, there is a possibility that other species have a role in the enriched consortium. Other proteinaceous fermenters might occur in low numbers that were not detected by denaturing HPLC and were outgrown during enrichment and isolation. Likewise, other hydrogen- and acetate-utilizing methanogens might be present in the initial enrichment that were not detected or isolated. However, the results of the study clearly demonstrate that this minimum five member consortium has a predominant role in the bioconversion process and can perform the role of the original consortium. Thus, the methanogenic microbial consortium defined here is useful as a complete consortium, without other methanogenic microorganisms present therein.

In order to maximize the methane production, temperatures for conversion of marine fish waste to biomethane using the methanogenic microbial consortium may range from about 20° C. to about 40° C. In certain embodiments, to obtain maximum rates of conversion of marine fish waste to biomethane using the methanogenic microbial consortium, the temperature may be controlled to range from about 26° C. to about 35° C.

In certain embodiments, the methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5, may be used for the conversion of marine fish waste to biomethane without the addition of trace metals, B-vitamins and additional phosphate and organic sulfur. Efficient conversion of the marine fish waste may be obtained without any requirement for these materials.

Although anaerobic bioconversion of saline RAS solid waste is a potentially cost effective methodology to achieve effective waste reduction, prior reports on biomass conversion of saline RAS sludge range between 1-54% of the theoretical yield (Zhang et al., 2013, *J. Environ. Manag.* 131, 44-54). This low efficiency has been attributed to the inability of microbial consortia that was poorly adapted to low C:N ratio and high salinity, most likely because inoculum originated from non-saline sources such as cow manure or municipal sewage sludge. It has now been unequivocally demonstrated that halotolerant consortia of microorganisms can be developed for bioconversion of saline fish waste with high efficiencies equivalent to those of non-saline waste systems and these consortia can be stably maintained in artificial medium without fish waste.

The 50 day incubation time required for complete biomass conversion in batch cultures is not indicative of rate in a flow through system as each batch experiment was initiated with a small inoculum and the observed rates reflect growth of the microbial population. In contrast, a continuous flow system would maintain a high steady state microbial population and higher rates of biomass conversion.

Establishment of an efficient, stable consortium for digesting solid organic waste in conjunction with in-line removal of nitrogenous waste by aerobic nitrification and anaerobic denitrification and annamox is desirable for creating and maintaining a near-zero recirculating mariculture system. The five component methanogenic microbial consortium described herein comprising two isolates of anaerobic fermentative bacteria and three isolates of archaea is suitable for use in recirculating mariculture systems.

An exemplary marine aquaculture system with varying characteristics, such as light exposure regimens, salinity, temperature, pH, etc. is provided in U.S. Pat. No. 6,443,097, incorporated herein by reference. Use of such aquaculture systems, as a result of its low waste production characteristics and its amenability to use of municipal water as a source of aqueous media for marine aquaculture processing, permits commercial fish-farming operations to be conducted in urban environments and similar locations where deployment of aquaculture production facilities had not been commercially practicable prior to development of such systems. Other marine aquaculture systems are known in the art and may be used for the marine aquaculture systems disclosed herein.

Marine aquaculture systems are broadly applicable to marine aquaculture production of a wide variety of marine species, including, but not limited to, gilthead seabream (*Sparus aurata*), haddock, reedfish (*Calamoichthys calabaricus*), sturgeon (*Acipenser transmontanus*), snook (*Centropomus undecimalis*), black sea bass (*Centropristis striata*), masu salmon, Atlantic salmon, rainbow trout, monkfish, sole, perch, tilapia, flounder, mahi mahi, striped bass, shad, pike, whitefish, swordfish, red snapper, barramundi, turbot, red drum, and the like.

A recirculated aquaculture system, while amenable to embodiment in various specific forms, typically comprises an assembly of tanks each containing an aqueous medium for a specific stage of the aquaculture process (broodstock conditioning, spawning, egg incubation, larval rearing, nursery rearing, and grow-out), with ancillary solids removal filters, biofilters having associated active microbial communities, oxygen (or oxygen-containing gas) sources, and automatic control unit(s) for monitoring and control of oxygen, salinity, temperature, photoexposure, pH and carbon dioxide in respective tanks of the aquaculture process system. The aquaculture process system may also include optional ancillary facilities, such as ozonation/disinfection units, foam fractionation (foam breaker or defoaming) units, brine generator units, automatic feeder units, biopsy facilities, harvesting/packaging facilities, etc.

The tanks that are used to contain the aqueous medium in carrying out the process of the invention may be of any suitable type, preferably being constructed of a corrosion-resistant material. The tanks may be covered to retard evaporation, or uncovered, as necessary or desirable in a given application of the invention.

The salinity of the aqueous medium in the tanks may be adjusted to the proper level using an electrochemical monitoring device such as a salinity probe and associated controls, or other of various suitable means known in the art for maintaining salinity at a desired value or within a predetermined operating range.

The tanks may be coupled to a suitable power supply, as necessary to power lighting systems and the like. The power supply associated with the lighting system in turn may be coupled to a monitoring and control module for the aquaculture system. Such monitoring and control module may be arranged to variably control the light to which the contents of the tank are exposed, specifically regulating the light intensity and the length of the photoperiod (the period of light exposure).

The monitoring and control module may also or alternatively be arranged to monitor and control other parameters of system operation, such as the water (aqueous medium) temperature, dissolved oxygen (DO) content of the water, pH of the water, feed (nutrient) dispensing, green water algal conditions, salinity, water flow rates into and out of the tank, etc., by appropriate coupling of the module with monitoring and control elements such as dissolved oxygen probes, thermocouples, pH sensors, flow monitors, flow control valves, salinity detectors, oxygen feed devices, acid/base dispensers, automated food dispensers, etc.

In operation of the aquaculture process system, aqueous medium may be pumped from the aquaculture tank by a system pump in a recirculation loop or flow circuit, for treatment outside the tank. For example, aqueous medium may be flowed from the tank to a filtration unit, such as a bead filter tank, in which suspended solids in the water are trapped by bead filtration media and removed from the aqueous medium.

Such filtration unit may for example be arranged to remove particulates having a particle size >20 microns. The bead filter is advantageously provided with electronic controls to effect periodic backflushing of the filter, e.g., cycle timer controls for backflushing at predetermined intervals, solids monitoring devices such as turbidity sensors, and/or other automated control means, the provision of which is within the skill of the applicable art.

The filtration unit removes sediment, and may have associated therewith a protein skimmer, to remove proteinaceous material floating to the top of the filtration tank.

In lieu of, or in addition to, bead filters, numerous other types of mechanical filters can be employed for solids removal, such as membrane filters, sedimentation chambers, clarifiers, centrifugal solids separators, filter presses, etc.

Upon completion of mechanical filtration, filtered water (filtrate) from the mechanical filter then may be flowed to a moving bed biofilter for nitrification under aerobic conditions, so that the ammonia ($NH_3$) or $NH_4^+$ present in the aqueous medium is converted to $NO_2$ and then to $NO_3$), with optional subsequent denitrification in a denitrification biofilter under anaerobic conditions. After optional denitrification, the aqueous medium can be re-oxygenated to provide a suitable level of dissolved oxygen therein, e.g., a concentration of at least 3 ppm, and preferably 3-7 ppm. The resultant treated water is recirculated to the aquaculture tank.

In the recirculation loop, water discharged from the filter can be selectively heated or cooled as necessary to maintain the aquaculture medium at a given temperature in the associated aquaculture tank. For example, such aqueous medium may be flowed to a heat exchanger, such as a shell-and-tube heat exchanger, in which the circulated aqueous medium is heated or cooled, as appropriate, by a heat exchange liquid, e.g., a glycol/water solution. The heat exchange liquid may be circulated through the passages of the heat exchanger from a source vessel, in which the liquid is maintained at a desired temperature, as necessary for the desired heat exchange heating or cooling of the aqueous medium.

In such manner, the water in the aquaculture tank can be maintained at a desired temperature appropriate to the specific fish species being grown in the process system.

In the recirculation flow circuit, a side stream loop may advantageously be provided, including a pump that is operated to flow the aqueous medium through a treatment unit in which dissolved organic species are removed by contact with ozone or oxygen. Such treatment unit optionally may be equipped with a protein skimmer, to remove floating proteinaceous matter from the surface of the liquid in the associated treatment unit tank(s). The treated water then may be flowed through a polishing chamber arranged for ion exchange, pH adjustment, and/or other treatment of the recycled aqueous medium, prior to its return to the aquaculture tank.

Overflow from any of the filters or tanks as well as waste solids from the filters in the aquaculture process system may be flowed to a waste tank where water and solids are treated with a disinfecting agent, such as chlorine or the like. The disinfected overflow/solids then may be discharged from the aquaculture system, e.g., into a municipal sewage system, aeration pond, or other receiving waters, for final disposition.

In certain embodiments, a modified UASB reactor as described in U.S. Patent Publication No. 2011/0039321, incorporated herein by reference in its entirety, may be used as the methanogenic bioreactor in a marine aquaculture system according the disclosure. A modified UASB differs from a standard UASB reactor in the formation of biofilms on a packing substrate or on fish waste particles themselves rather than immobilization of sludge by formation of large microbial aggregates into distinct granules, as occurs in a standard reactor.

Figure 7:
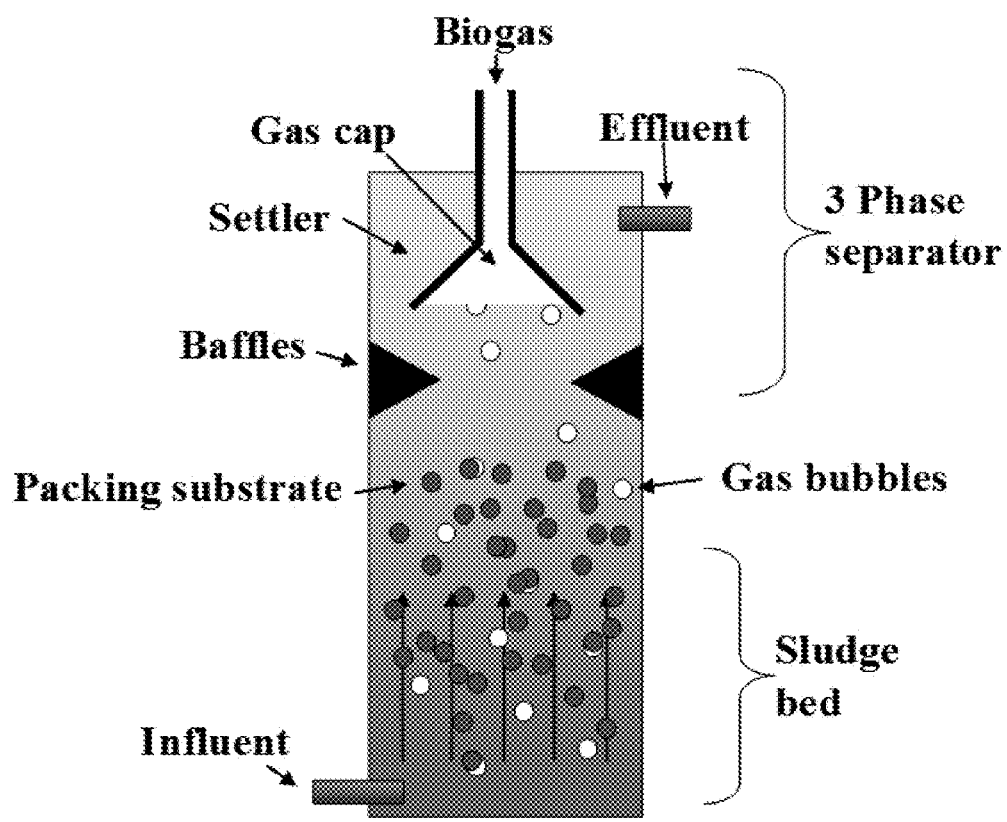
FIG. 7 is a model of an exemplary upflow anaerobic sludge blanket (UASB) reactor useful as a methanogenic bioreactor in marine aquaculture systems as described in U.S Patent Publication No. 2011/0039321.

Such modified UASB reactor may include an inlet for ingress of the waste-containing aqueous medium, and contains a bottom layer of sludge packed into a "sludge bed," a sludge blanket covered with packing substrate and an upper liquid layer, as shown in FIG. 7. Near the top of the reactor, baffles are provided to direct any biogas generated by anaerobic degradation of the sludge to the gas cap and out of the top of the vessel. Settler screen(s) are provided to separate the sludge from the treated aqueous medium and an outlet is provided for egress of the treated aqueous medium.

In the modified UASB reactor described herein, the "packing substrate," also referred to as a "packing material" may be used to immobilize the organic solids. The packing material present in the modified reactor preferably comprises a material with a high surface-to-volume ratio. The packing material serves as a substrate for formation of microbial biofilms comprising a methanogenic consortium of microorganisms (fermenters, acetogens and methanogens) and improves the methane production by the consortium by providing a high surface area. Alternatively, the modified UASB reactor may be operated without packing material wherein the biofilms form on fish waste particles themselves. The system may further operate where there is any surface that allows the formation of a biofilm In certain embodiments, production of methane is obtained from marine fish waste utilizing a modified UASB reactor with a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5. Saline fish waste-containing aqueous medium is fed into the modified reactor from the influent and flows upward through the sludge bed and packing substrate. The organic solids within the aqueous medium affix to the packing substrate and form microbial biofilms with maximized surface area allowing for reaction with additional substrates, resulting in generation of methane.

Figure 8:
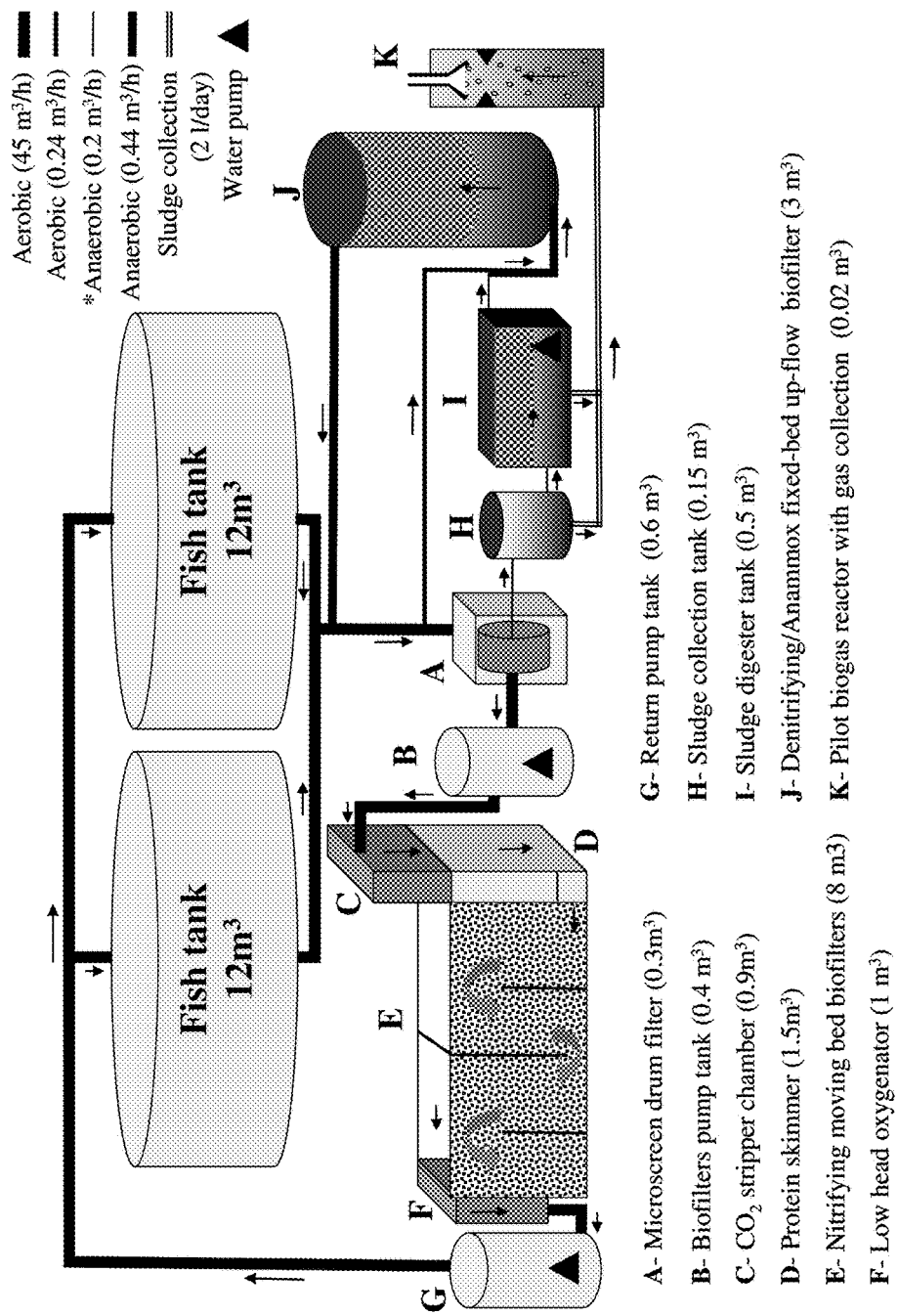
FIG. 8 illustrates an exemplary configuration of a recirculating aquaculture system with an integrated UASB bioreactor for methane production as part of its anaerobic water treatment loop as described in U.S Patent Publication No. 2011/0039321.

Thus, the disclosure provides for a marine recirculating aquaculture process system with a modified UASB reactor integrated therein. An exemplary recirculating marine aquaculture system with an integrated modified UASB reactor is shown in FIG. 8.

In a certain embodiment, the disclosure provides an upflow anaerobic digestion generation system, including an upflow reactor as described which utilizes a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5.

In a preferred embodiment, the modified UASB reactor would include an inlet at a lower portion of the reactor and an outlet at an upper portion of the reactor. The reactor would also preferably contain a saline medium and a bed of sludge solids in a lower portion. Additionally, within the reactor would be a plurality of support bodies having methanogenic biofilms thereon. The system would include a gas recovery assembly adapted to recover methane-containing gas generated by said methanogenic biofilms as a result of anaerobic digestion of said sludge solids.

A marine aquaculture process facility may include salt water storage for the aqueous medium used in the process. Salt water may be produced in the aquaculture facility using a brine generator, with trace mineral introduction and saltwater mixing in a mixing chamber, e.g., to form a saline aqueous medium at the salinity of natural seawater, or higher. The resultant saline aqueous medium then can be used in the process, at full strength or in diluted (hyposaline) form, as may be variously desired in the respective steps of the aquaculture process.

The marine aquaculture system may comprise appropriate flow circuitry in the form of pipes, conduits, manifolds, flow control valves, restricted flow orifice elements, valve actuators and controllers (which may be of any appropriate type, including elements such as pneumatic actuators, electromechanical actuators, solenoid valves, etc.) and the flow circuitry may include or be operatively coupled to a central controller unit or assembly.

In operation, the aqueous medium from the aquaculture tank preferably is circulated in a closed recirculation loop to an aqueous medium treatment complex (e.g., comprised of equipment such as bead filters, biofilters, ozonation units, protein skimmers, etc.) and recirculated to the aquaculture tank after treatment in the exterior recirculation loop.

In this manner, the process system is advantageously arranged to provide a desired volumetric turn-over frequency of the aqueous medium in the operation of the system, with flow from the aquaculture tank through the associated liquid recirculation loop and back to the aquaculture tank, with waste removal and make-up water addition as required. By appropriate arrangement of the recirculation loop and component pump(s), an appropriate turn-over rate of the aquaculture tank liquid volume may be effected for the specific operation being carried out in such tank. For example, the process can be operated to replenish the entire volume of water in the aquaculture tanks at a rate in a range of from about 1.5 to about 5 times an hour, e.g., 2 to 4 times an hour, or 3 to 4 times an hour, as may be desired in various illustrative embodiments.

The liquid recirculation loop associated with the aquaculture tank desirably includes a biofilter, preferably containing microbial support media in a moving bed filter that is maintained in suspension in the tank liquid. Liquid circulation in the biofilter may be effected by diffusing air through a porous element, such as a rubber disk membrane, to cause the microbial support media to tumble and mix. The injection of gas and resultant gas-induced mixing provides increased contact between the microbial communities in the biofilter and the various dissolved metabolites. This in turn increases the cleansing action of the biofilter in treating the large volumes of water that are recirculated in the aquaculture system to achieve high efficiency operation.

Each aquaculture tank in the aquaculture process system preferably is computer monitored to control temperature, pH, dissolved oxygen, salinity, flow rates, light intensity and length of photoperiod at specific preferred optimal values or in specific optimal ranges, as appropriate to the particular aquaculture process and fish species involved. In the biofilters, monitoring advantageously is carried out to maintain microbial flora on the biofilter substrate elements in populations appropriate to high-rate purification of the aqueous medium in the high flow rate recirculation loop.

For such purpose, appropriate sensing, monitoring and control elements may be interconnected with a CPU or other computer or automatic controller/monitoring unit, to provide an integrated monitoring and control module, e.g., for monitoring and controlling process parameters such as flow rates, photoexposure, dissolved oxygen concentration, temperature, pH, etc., and/or for effecting process operations, such as backwashing of system filters, filling/emptying of process tanks, dispensing of feed/nutrient material, actuating heating/cooling systems, etc.

In the entire aquaculture process, electronic controls may be employed for backflushing filters, for monitoring and controlling flow rates, dissolved oxygen concentration, temperature, pH, etc., using a microprocessor or computer system. Waste comprising overflow and solids sedimented or backwashed from the filters may be processed by disinfection and final discharge to sewer or other disposition or treatment, as previously described.

In optimal operation, a marine aquaculture process may be conducted with less than 10% daily water exchange (daily water exchange meaning the water that is introduced to the aquaculture system as net make-up, and the water that is discharged from the system as net effluent to the waste disposal system). The aquaculture process system in such respect is a "closed" recirculating aquaculture system, since the net exchange of water with the external environment during normal operation of the system is extremely low. Such low level of net water consumption is enabled by the recirculated and continuously purified character of the water. The net waste generation is minimized, and net waste produced in the operation of the facility can be readily accommodated by local sewer, septic and wastewater treatment facilities.

The disclosure includes a closed, recirculating marine aquaculture system comprising brackish or salt water comprising marine fish waste, a tank comprising a marine species, and a methanogenic bioreactor comprising a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5.

The closed, recirculating marine aquaculture system may further comprise equipment as described above in various combinations, based on the requirements of the brackish or saltwater, the composition of the marine fish waste and/or the type of marine species, among other factors.

The disclosure, as variously set out herein in respect of various described features, aspects and embodiments, may in particular implementations be constituted as comprising, consisting, or consisting essentially of, some or all of such features, aspects and embodiments, as well as elements and components thereof being aggregated to constitute various further implementations of the disclosure. The disclosure contemplates such features, aspects and embodiments in various permutations and combinations, as being within the scope of the disclosure. The disclosure may therefore be specified as comprising, consisting or consisting essentially of, any of such combinations and permutations of these specific features, aspects and embodiments, or a selected one or ones thereof.

By way of example, the disclosure may include a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5. Alternatively, the methanogenic microbial consortium may consist essentially of (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5 such that other methanogenic microorganisms are not present in the consortium. Further alternatively, the methanogenic microbial consortium may consist of (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5. Such methanogenic microbial consortium may be the only microbial consortium in a bioreactor.

The advantages and features of the disclosure are further illustrated with reference to the following examples, which are not to be construed as in any way limiting the scope of the disclosure but rather as illustrative of the disclosure herein.

EXAMPLES

Materials and Methods

1. Fish Waste Sludge

Fish waste sludge solids samples used for developing and maintaining inoculum were obtained from the sludge collection tank of a 24 m³ recirculating aquaculture system supporting growth of gilthead seabream (*Sparus aurata*) as described previously (Tal, 2009, Aquaculture 286, 28-35). The system included two 12 m³ tanks each stocked with approximately 2100 fish that were grown from an average weight of 50 to 450 g. Sludge samples consisting of approximately 2% solids were harvested from a settling tank immediately upstream of a biogas reactor and had an average chemical oxygen demand (COD) of 21 g $l^{-1}$. Samples were used immediately after harvesting or stored in sealed bottles at 4° C. prior to use. For culture medium, sludge was concentrated by centrifugation to 50% of its original volume to create a 2× stock and added to an equal volume of medium to achieve a final COD of 21 g $g^{-1}$.

2. Enrichment of Sludge Digesting Consortia

Growth medium consisting of buffered artificial seawater was prepared anaerobically under a $N_2$—$CO_2$ (4:1) atmosphere as described previously (Sowers et al., 1995, Robb, F. T., Sowers, K. R., DasSharma, S., Place, A. R., Schreier, H. J., Fleischmann, E. M. (Eds.), Archaea: A Laboratory Manual. Cold Spring Harbor Laboratory Press, Plainview, pp. 15-48). All gases were passed through a column of reduced copper filings at 350° C. to remove traces of $O_2$. Artificial seawater (Zohar et al., 2005) diluted to 15 g $l^{-1}$ with deionized water was amended with 1 g $l^{-1}$ $Na_2HCO_3$ as a buffer and 1 mg $l^{-1}$ resazurin (7-hydroxy-3H-phenoxazin-3-one 10-oxide) as a redox indicator. The pH was adjusted to 7.4. The medium was dispensed (250 mL) into a 700-ml safety coated reagent bottle and sealed under 101 kPa $N_2$—$CO_2$ (4:1) with a screw cap containing a butyl rubber septum core.

An equal volume (250 mL) of 2× concentrated fish waste sludge solids was added to the medium as inoculum and substrate in the primary enrichment culture; thereafter 250 ml of 2× concentrated fish waste solids was added as substrate to 250 ml buffered seawater immediately prior to inoculation with 50 ml of inoculum from the previous enrichment culture. Bottles were incubated in a rotary shaking incubator at 26° C. and 25 rpm. Enriched inoculum was maintained by sequential transfers every 2-3 months.

3. Isolation and Reconstitution of Microorganisms from Consortium

Microorganisms were isolated from enrichment cultures by plating on agar-solidified anaerobic medium as described previously (Apolinario and Sowers, 1996) with modifications described below. Fermentative bacteria were isolated in medium that contained the following components in g $l^{-1}$ of artificial seawater: peptone, 5; cysteine, 0.25; resazurin, 0.0001. Oxygen was removed from the medium by sparging with $N_2$—$CO_2$ (4:1) through a sintered glass gas distribution tube. The degassed medium was then transferred to an anaerobic glove box (COY Laboratory Products) containing an atmosphere of $N_2$—$CO_2$—$H_2$ (16:4:1) and filter sterilized with a 0.45 μm disposable filter unit (Nalgene). Aliquots of 150 ml deionized water degassed by sparging with $N_2$ were dispensed into 700 ml safety coated reagent bottles (Wheaton) each containing 3 g Bacto™ agar (BectonDickinson). The bottles were sealed under a $N_2$ headspace as described above and sterilized by autoclaving at 121° C. for 20 min. After autoclaving the agar was cooled to 55° C. in a water bath Immediately prior to use the agar was transferred to an anaerobic glove box, combined with 150 ml of medium and poured into 15×100 mm petri plates. The final salinity of the solidified medium was 15 ppt.

Plates were dried in the glove box for two days in a relative humidity of 30-35%. Ten-fold serial dilutions of inoculum from an enrichment culture were created in 9 ml aliquots of liquid medium and 1 ml of each dilution was inoculated onto solidified medium by spreading. Plated cultures were incubated at 30° C. in stainless steel anaerobe jars (Torbal) under $N_2$—$CO_2$ (4:1) and 0.003% (v/v) $H_2S$ generated from $Na_2S$ as described previously (Apolinario et al., 1996, *FEMS Microbiol. Lett.* 145, 131-137). Isolated colonies were further purified by streaking on solidified medium.

Methanogenic archaea were isolated on agar-solidified E-Cl medium (estuarine medium without sulfate containing the following components in grams per liter (final concentration) of basal medium: NaCl, 8.4; $MgCl_2 \cdot 6H_2O$, 3.95; KCl, 0.27; $CaCl_2 \cdot 2H_2O$, 0.05; see, Berkaw et al., *Appl. Environ. Microbiol.* 62, 2534-2539, 1996) with a reduced $Na_2S$ concentration. Oxygen was removed from the medium by sparging with $N_2$—$CO_2$ (4:1) through a sintered glass gas distribution tube. Aliquots of 100 ml were transferred to 125 ml serum vials each containing 1.25 g Bacto™ agar and 0.0025% (w/v) $Na_2S \cdot 9H_2O$.

For isolation of aceticlastic methanogens 0.1 M sodium acetate was added to the vial. The medium was sealed under a $N_2$—$CO_2$ (4:1) headspace with butyl rubber septa secured with aluminum crimp seals and sterilized by autoclaving at 121° C. for 20 min. After autoclaving the agar was cooled to 55° C. in a water bath Immediately prior to use the agar medium was transferred to an anaerobic glove box, and poured into 15×100 mm petri plates. The plates were dried as described above. Ten-fold serial dilutions of 1 ml inoculum from an enrichment culture were created in 9 ml aliquots of liquid medium prepared anaerobically in Balch-style anaerobe tubes and 1 ml of each dilution was inoculated onto solidified medium by spreading. Plated aceticlastic cultures were incubated at 30° C. in stainless steel anaerobe jars under $N_2$—$CO_2$ (4:1) and 0.003% (v/v) $H_2S$ generated from $Na_2S$ as described above. For hydrogen-utilizing methanogens the $N_2$—$CO_2$ atmosphere was replaced with $H_2$—$CO_2$ (4:1) to 200 kPa. $H_2$—$CO_2$ was replenished when depleted to 101 kPa or less as indicated by a pressure gauge.

Isolated colonies were further purified by streaking on solidified medium containing 100 mg $l^{-1}$ vancomycin. Isolates were maintained in liquid ECl medium under an atmosphere of 101 kPa $N_2$—$CO_2$ (4:1) or 202 kPa $H_2$—$CO_2$ (4:1).

The consortium was reconstituted by transferring the isolates to ECl medium containing 5 g $l^{-1}$ Brain Heart Infusion broth (Difco) for three sequential transfers. To compare the efficiency of the reconstituted consortium with the enriched consortium 5 ml of culture were inoculated into to 50 ml ECl medium containing fish waste sludge at a final COD concentration of 21 g $l^{-1}$. Efficiency was determined by measuring the biochemical methane potential as described below.

4. Enrichment Characterization

The effect of selected treatments on biological methane potential was tested by amending the buffered growth medium described above. To determine the effect of trace nutrients the following components were added to buffered artificial seawater: cysteine (0.025% w/v), trace metals stock (1% v/v) and B-vitamin stock solutions (1% v/v) (Wolin et al., 1963, *J. Biol. Chem.* 238, 2882-2886). To determine the effect of trace metals specifically required by methanogenic Archaea the following components were added to buffered artificial seawater: $FeSO_4$ (5 μm), $CoCl_2$ (0.5 μm) and $NiCl_2$ (0.5 μm). To reduce the sulfate concentration of the medium magnesium sulfate ($MgSO_4 \cdot 7H_2O$) was substituted with the molar equivalent of magnesium chloride ($MgCl_2 \cdot 6H_2O$). To increase the COD:N ratio of the sludge carboxymethyl cellulose (CMC) was added (1% w/v; CMC=6,560 ppm).

5. Biochemical Methane Potential (BMP)

The efficiency of biomass conversion by the sludge enrichment was determined using a modification of the BMP assay (Moody et al., 2009, 44th Croatian and 4th International Symposium on Agriculture, pp. 930-934). Buffered artificial seawater (50 ml) was dispensed into 160-ml serum bottles and sealed under 101 kPa $N_2$—$CO_2$ with butyl rubber stoppers secured with aluminum crimp seals. Medium was inoculated with 50 ml 2× fish waste sludge solids and 5 mls of enriched inoculum, then re-sealed under $N_2$—$CO_2$ (4:1). After equilibration for 30 minutes the headspace was sampled for methane using a 100 μl gas-tight syringe with valve as described below. Bottles were incubated in a rotary shaking incubator at 26° C. and 25 rpm. During the first three weeks after transfer the headspace was sampled without subsequent purging. Thereafter, the bottles were purged with $N_2$—$CO_2$ after each sampling to prevent changes in pH as a result of excess carbon dioxide. The methane reading was added to the prior methane value to determine total methane production over the course of the experiment.

6. Analytical Methods

Methane was assayed with a HP5890 gas chromatograph (Hewlett Packard) equipped with a flame ionization detector and stainless steel column (0.32×182.88 cm) packed with silica gel (80/100 mesh; Supelco). The column oven was operated at 110° C. with He as the carrier gas. Purified methane (Methane, ultra-high purity, Matheson Tri Gas) was used as a standard. Chemical oxygen demand (COD) was determined using a HACH High Range plus COD (0-15,000 ppm range) test kit following manufacturer's directions. Samples were diluted with water to 25% of the original concentration prior to analysis. Total Nitrogen (TN) was determined using a High Range Total Nitrogen HACH test kit (Hach Method 10072, 10-150 mg l$^{-1}$ range). Samples were diluted with water to 6.7% of the original concentration prior to analysis. Total organic carbon (TOC) was determined using a TOC HACH test kit (Hach Method 10128HR, 100-700 mg L$^{-1}$ range). Samples were diluted with water to 10% of the original concentration prior to analysis. Total organic carbon was further measured using a Shimadzu TOC analyzer (by instrument) with a solids sample module (TOC-5000A and SSM-5000A) by combustion at 900° C. after removal of inorganic carbon with hydrochloric acid.

7. DNA Extraction and Amplification

DNA was extracted by adding 0.25 g of culture containing suspended sludge particles to a PowerBead microfuge tube of a Power Soil® DNA Isolation Kit (MOBIO Laboratories, Inc.) as described previously (Payne et al., 2011, *Environ. Sic. Technol.* 45, 8772-8779). The total bacterial community was monitored by amplification of the 16S rRNA genes with universal primers 341F/907R (Lane et al., 1985, *Proc. Natl. Acad. Sci. U.S.A.* 82, 6955-6959; Muyzer et al., 1993, *Appl. Environ. Microbiol.* 59, 695-700). PCR amplification conditions were as follows: denaturation at 95° C. for 3 minutes; 35 cycles at 95° C. for 45 seconds; annealing at 45° C. for 45 seconds; extension at 72° C. for 1 minute, followed by a final extension at 72° C. for 5 minutes. The 0.56 kb PCR product was purified on a 1.2% agarose gel. Methanogenic archaea were monitored by amplification of methyl-coenzyme M reductase (MCR) with primers ME1/ME2 (Hales et al., 1996). PCR amplification conditions were as follows: denaturation at 95° C. for 5 minutes; 35 cycles at 95° C. for 45 seconds; annealing at 50° C. for 30 seconds; extension at 72° C. for 1 minute and a final extension at 72° C. for 3 minutes. The PCR product (0.75 kb) was purified on a 1.2% agarose gel. DNA was eluted from the excised band with 50 µl of PCR grade water and quantified with a NanoDrop 1000 Spectrophotometer (ThermoScientific). Extracted DNA samples had an A260/280 ratio of ≥1.6 and an A260/230 ratio of ≥2.0. All DNA samples were diluted to 2 ng/µl in TE buffer.

8. Community Identification Using Denaturing HPLC

A WAVE 3500 HT denaturing gradient HPLC system (Transgenomic, Inc.) equipped with a fluorescence detector was used to separate and identify different 16S rRNA gene products as described previously (Payne et al., 2011, *Env. Sci Technol.* 45, 8772-8779). PCR amplification product peak fractions from universal 16S primers 341F/907R and MCR primers ME1/ME2 were collected and sequenced as described previously (Kjellerup et al., 2008, *Environ. Microbiol.*, 10, 1296-1309). Sequences were submitted to the National Center for Biotechnology Information's (NCBI) Basic Local Alignment Search Tool (BLAST) (Altschul et al., 1990) to determine similarity with other 16S rDNA and MCR gene sequences.

9. Nucleotide Sequence Accession Numbers

The 16S rRNA gene sequences for 16S rRNA genes from strains isolated were submitted to GenBank under the following accession numbers: *Dethiosulfovibrio* sp. EA-F2, KT799836 (SEQ ID NO: 1); *Fusobacteriacea* EA-F3, KT799837 (SEQ ID NO: 2); *Methanogenium* sp. EA-M3, KT799838 (SEQ ID NO: 3); *Methanoplanus* sp. EA-M7, KT799839 (SEQ ID NO: 4); *Methanosarcina* sp. EA-M15, KT799849 (SEQ ID NO: 5).

Results

1. Characterization of Solid Waste from the Recirculating Aquaculture System (RAS)

The RAS used as a source of sludge for this study was described previously (Tal, 2009, Aquaculture 286, 28-35). Sludge collected with a microscreen drum filter (60 µm screen mesh; Hydrotech, Model 801, Vellinge, Sweden) and backwash system that used tank water was collected from an 800 l conical settling tank that had a hydraulic retention time of four hours. Sludge for development and feeding of microcosm digestors was collected from the bottom of the settling tank and used within 1 day for all experiments. The sludge consisted of fish waste (feces), which has an apparent digestibility coefficient for organic matter by seabream of 69% (Lupatsch et al., 1998, *Aquat. Living Resour.* 11, 265-268), and uneaten Europa 15 and 18 pellets (3, 4, 6 mm; Skretting's) consisting of not less than 50% protein and 18% fish oils. The characteristics of the sludge are shown in Table 1.

TABLE 1

| Parameter | Value |
| --- | --- |
| COD | 20.8 ± 1.3 g l$^{-1}$ |
| TN | 1.4 ± 0.3 g l$^{-1}$ |
| TOC (by instrument) | 7.3 ± 0.0 g l$^{-1}$ |
| pH | 7.4 |
| C:N | 5.2:1 |
| COD:N | 14.7:1 |
| salinity | 15 g l$^{-1}$ |
| COD:SO$_4$ | 20.5:1 |

2. Development of Methanogenic Consortium for Biomass Conversion of Waste Material The rates and extent of biomass conversion to biogas in 500 ml enrichment cultures are shown in FIG. 1. Prior to digestion the sludge was nearly black in color and had a thick consistency with particles remaining suspended in liquid (FIG. 9). After digestion the sludge was light brown in color with a sandy consistency that settled out of the liquid phase. The rate of conversion in the initial inoculum was only 41.2 mmol CH$_4$ kg COD$^{-1}$ d$^{-1}$, but increased 10-fold to a maximum rate of 428 mmol CH$_4$ kg COD$^{-1}$ d$^{-1}$ after seven sequential transfers. The digestible fraction of fish waste averaged 90% of the total estimated yield based on COD. This high rate of activity and a reduced lag time of 5 days was consistent for subsequent 10% (vol/vol) transfers of enriched inoculum.

3. Identification of Factors Affecting Biological Methane Potential

Figure 2:
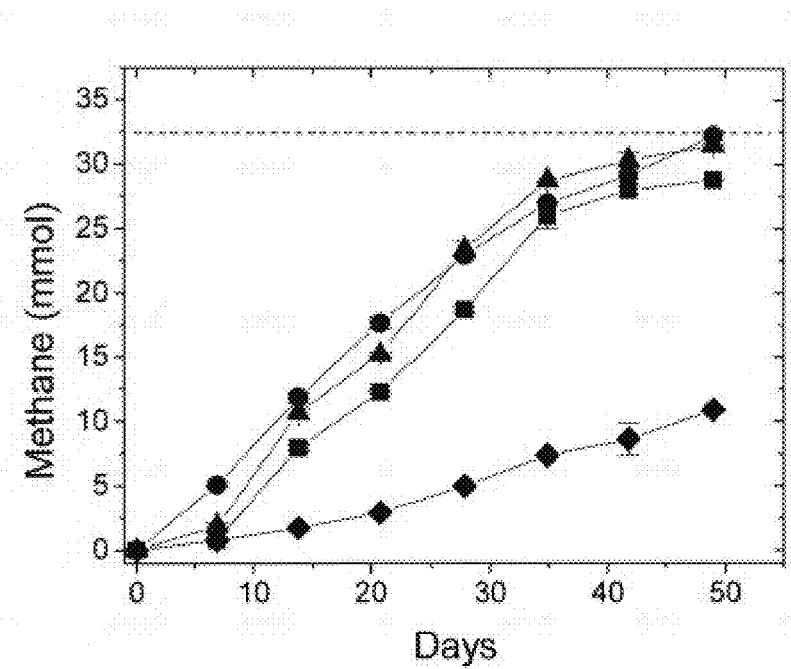
FIG. 2 is a graphical representation of the effect of temperature on rates of methane production by fish sludge enrichment. The graph shows methane production during incubation at 20 (♦), 26 (■), 30 (▲) and 35 (●) ° C. The dashed line represents estimated maximum methane yield from total COD of sludge. Values are means and standard deviations for three replicate culture samples.

The chemical composition of the solid waste was modified to identify factors that might limit the rates and maximum biomass conversion. Addition of a mixture of 12 trace metals required by bacteria and ten-fold increase in Fe$^{+2}$, Ni$^{+2}$ and Co$^{+2}$ required by methanogenic archaea for several cofactors and redox enzymes did not have an effect on the rate of methanogenesis or BMP. Addition of cysteine, added as an organic sulfur source, and eight B-vitamins did not increase methane yield and actually slightly reduced the rate of methanogenesis from 428 to 402 mmol CH$_4$ kg COD$^{-1}$ d$^{-1}$. Increasing COD:SO$_4$ from 21:1 by substituting Cl$^-$ for SO$_4^{-2}$ in the artificial seawater reduced the conversion of biomass to methane from 428 to 316 mmol CH$_4$ kg COD$^{-1}$ d$^{-1}$. The effect of increasing the COD:N from 15:1 to 39:1 was also examined by addition of starch and methylcellulose. Starch had no observable effect. Increasing the COD with methylcellulose from 20,840 mg $l^{-1}$ to 55,000 mg $l^{-1}$ decreased the rate of methanogenesis from 428 to 185 mmol $CH_4$ kg $COD^{-1}$ $d^{-1}$ and the final yields were 89 and 91%, respectively, of the estimated methane yield (FIG. 2).

Figure 3:
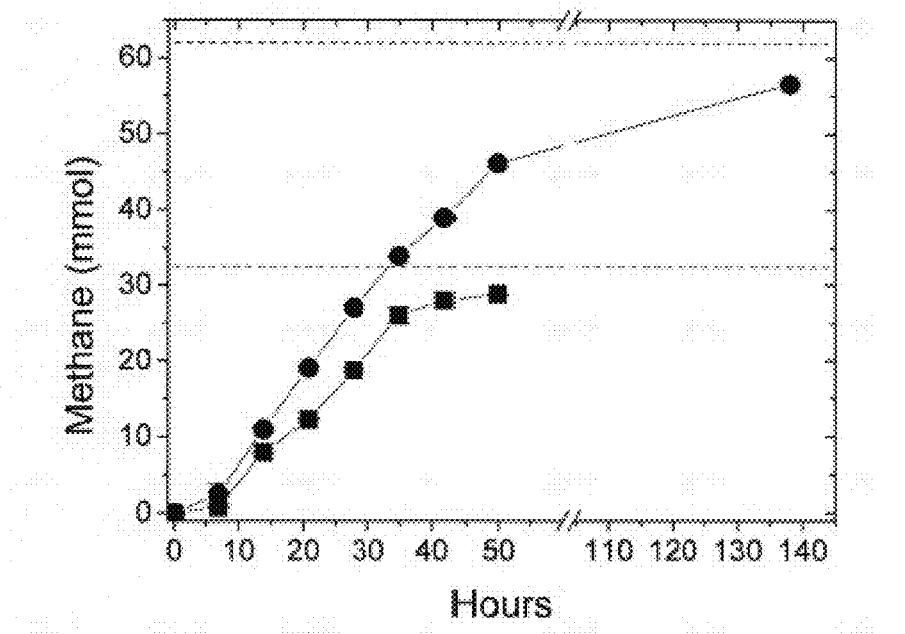
FIG. 3 is a graphical representation of the effect of carbon to nitrogen ratio on rates of methane production by fish sludge enrichment. The graph shows methane production during incubation with sludge with native C:N ratio of 15:1 (■) and after increasing the C:N ratio to 39:1 (●). The dashed line represents estimated maximum methane yield from total COD of sludge and carbon amendment. Values are means and standard deviations for three replicate culture samples.

Temperature was shown to have an effect on the amount of methane produced (FIG. 3). Methane production decreased by 62.2% when bottles were incubated at 20° C. instead of the ambient system temperature of 26° C. However, methane production increased by 9.3% at 30° C. and by 11.8% when at 35° C., compared to 26° C.

4. Characterization of the Microbial Consortium

DNA was isolated from the initial enrichment after incubation for two months and from a culture enriched by six sequential transfers over a period of 12 months. Phylotypes were separated by denaturing HPLC and DNA from individual peaks was collected and sequenced.

Five predominate bacterial phylotypes with highest identity to anaerobic fermenters *Odoribacter* spp., *Bacteroides* spp. and *Tindallia* spp. were detected in the initial enrichment culture (FIG. 4A, FIG. 4B). Since 16S rRNA gene detection using universal primers is often less sensitive to archaea, a primer set was used that is specific for the gene encoding methyl coenzyme M reductase, which is shared universally by all described methanogens. Using the archaeal primers only two phylotypes with highest sequence identities to acetate-utilizing *Methanosarcina* spp. were detected in the initial enrichment (FIG. 4A, FIG. 4B). In the highly enriched culture five predominant phylotypes were detected, but there was a shift in the chromatograms (FIG. 4A, FIG. 4B). Two bacterial phylotypes with highest sequence identity to the anaerobic fermenters *Fusobacterium* spp. and *Dethiosulfobacter* spp., and two archaeal phylotypes with sequence similarity to *Methanosarcina* spp. were detected with 16S rRNA gene primers. Using MCR primers three archaeal phylotypes with highest sequence identities to acetate-utilizing *Methanosarcina* spp. and hydrogen-utilizing *Methanogenium* spp. and *Methanoplanus* spp. were detected.

5. Isolation and Reconstitution of the Methanogenic Consortium

Five microorganisms were isolated from the highly enriched culture sequentially transferred in medium with fish waste sludge. Table 2 lists the microorganisms isolated from the fish waste enrichment culture:

TABLE 2

| Isolate | 16S Sequence similarity to reported species | Growth substrate |
| --- | --- | --- |
| Fusobacteriacea EA-F3 | 92-96% | Peptone |
| *Dethiosulfovibrio* sp. EA-F2 | 99% | Brain heart infusion |
| *Methanogenium* sp. EA-M3 | 99% | $H_2$—$CO_2$ |
| *Methanoplanus* sp. EA-M7 | 100% | $H_2$—$CO_2$ |
| *Methanosarcina* sp. EA-M15 | 100% | acetate |

A rod shaped bacterium (EA-F3) with high sequence similarity to species in the *Fusobacteriacea* was isolated on and subsequently maintained in E-Cl medium containing peptone. A *vibrio*-shaped bacterium (EA-F2) with high sequence identity to *Dethiosulfovibrio* spp. was isolated on solidified E-Cl medium containing peptone, but required brain-heart infusion medium for subsequent maintenance. Species in both genera are obligate fermentative bacteria capable of utilizing peptides and amino acids for growth (Staley et al., 2011, Phylum XIX. Fusobacteria, in: Krieg, N. R., Parte, A., Ludwig, W., Whitman, W. B., Hedlund, B. P., Paster, B J., Staley, J. T., Ward, N., Brown, D. (Eds.), Bergey's Manual of Systematic Bacteriology. Springer, New York, N.Y., pp. 747-765; Surkov et al., 2001, *Int. J. Syst. Evol. Microbiol.* 51, 327-337).

Two methanogenic archaea were isolated with hydrogen as the electron donor: a rod shaped archaeon with high sequence identity to *Methanogenium* spp. (EA-M3) and a disc-shaped archaeon with sequence identity to *Methanoplanus* spp. (EA-M7). Species in both genera utilize only hydrogen or formate for growth and methanogenesis (Sowers, 2009). An irregular coccus with sequence identity to *Methanosarcina* spp. (EA-M 15) was isolated with acetate as the growth substrate. Species within all three genera have been isolated from saline environments (Sowers, 2009, Methanogenesis, in: Schaechter, M. (Ed.), Encylopedia of Microbiology, $3^{rd}$ Ed. Elsevier/Academic Press, pp. 265-286).

Figure 5:
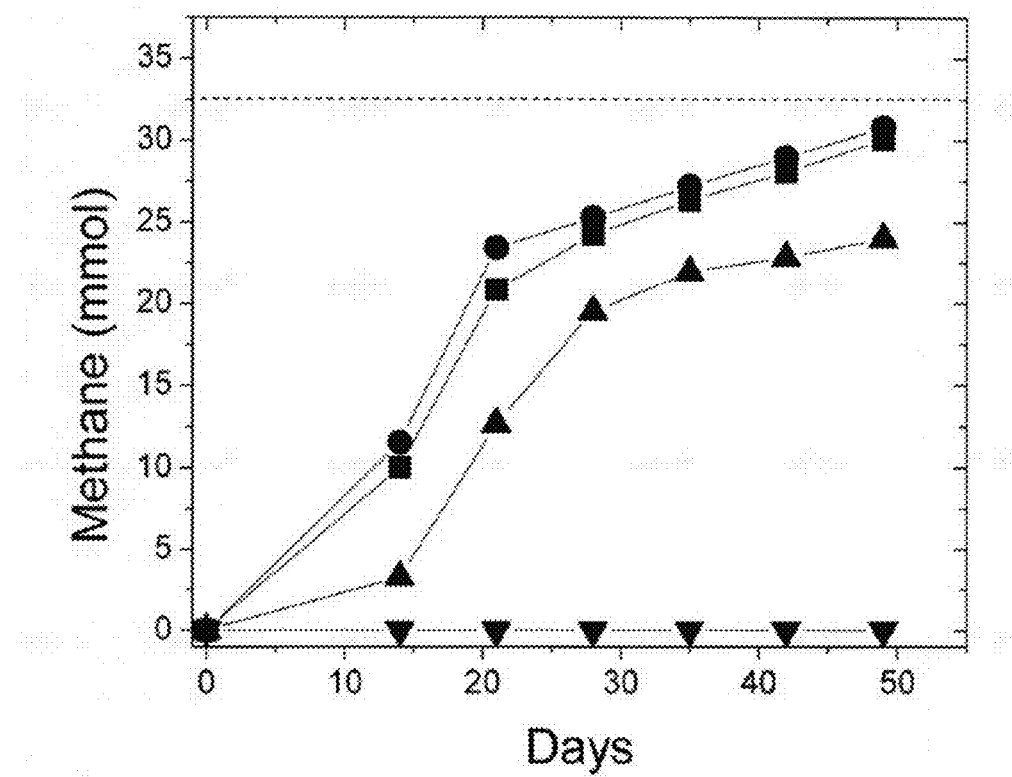
FIG. 5 is a graphical representation of the conversion of fish waste to methane by enrichment culture and reconstituted consortium. The graph shows methane production from sterilized fish waste uninoculated (▼) and inoculated with enriched culture (●), reconstituted consortium from BH1 medium (▲) and reconstituted consortium after one transfer in sterile fish waste (■). The dashed line represents estimated maximum methane yield from total COD of sludge and carbon amendment. Values are means and standard deviations for three replicate culture samples.

The two fermentative bacteria and three methanogenic archaea were reconstituted as a consortium in E-Cl medium containing brain heart infusion broth. Successful reconstitution was confirmed by production of methane as the methanogens cannot grow alone in complex medium such as brain heart infusion or peptone, but require fermentative bacteria to generate hydrogen and acetate for methanogenesis (data not shown). Conversion of sterile fish waste sludge to methane was compared between enriched inoculum and the reconstituted consortium to determine whether the principal species required for optimal methanogenesis were identified (FIG. 5). The reconstituted consortium transferred from artificial medium exhibited a greater lag and an overall reduction in total methane production by approximately 20% compared with enriched inoculum. However, one sequential transfer of the reconstituted consortium in medium containing sterile fish waste completely restored the efficiency of bioconversion to that observed for the enriched inoculum. Profiles of the of the phylotypes in enriched inoculum and reconstituted consortium with sterile fish waste were similar indicating that the reconstituted consortium included the critical species required for efficient bioconversion of the marine fish waste (FIG. 6A, FIG. 6B).

Figure 10:
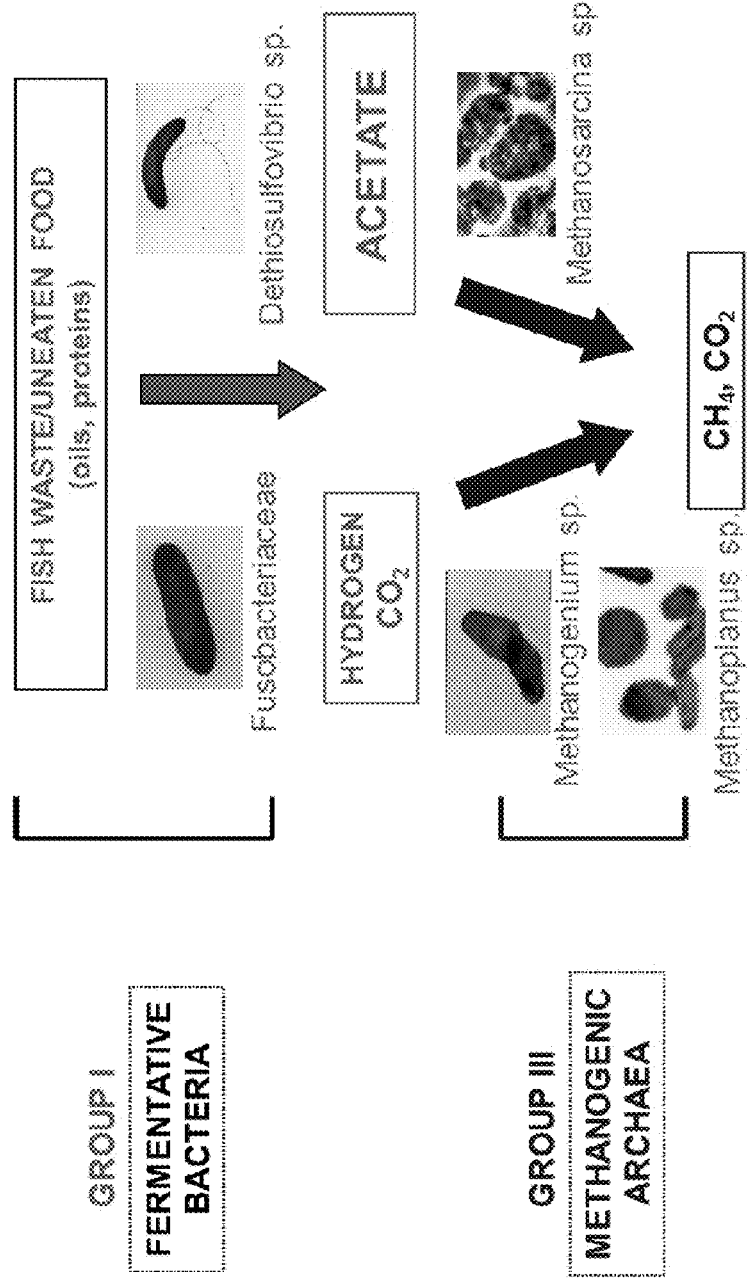
FIG. 10 is a flow diagram illustrating how the methanogenic consortium of the disclosure, developed for marine fish waste, works in, for example, a marine aquaculture system.

FIG. 10 is a flow diagram of how the methanogenic consortium works in an aquaculture system.

As detailed, a methanogenic consortium was enriched by sequential transfer in seawater with fish sludge from the marine RAS to develop a biomethane generating consortium that was native to saline fish waste. Trace elements such as iron, cobalt and especially nickel, which are required for cofactors in methanogens, have been reported to increase methane production in anaerobic digestors (Demirel et al., 2011, *Biomass Bioenergy* 35, 992-998). In addition B-vitamins are required by species of *Methanogenium* and *Methanosarcina* (Jarrell et al., 1988, *Can J. Microbiol.* 34, 557-576). In the system tested (examples) the addition of trace metals, B-vitamins and additional phosphate and organic sulfur, however, did not improve the rates or total methane produced in batch experiments using fish waste.

The results indicate that both fish waste and undigested fish meal likely provide a rich medium containing saturating concentrations of essential growth factors. High sulfate concentration in marine sludge has the potential to reduce methane production because sulfate reducing bacteria have a greater affinity for acetate and hydrogen as well as a small thermodynamic advantage, compared to the methanogens (Chen et al., 2008, *Bioresour. Technol.* 99, 4044-4064). In addition to substrate competition, the product of sulfate reduction, H$_2$S, can possibly reach the toxicity thresholds for methanogens (Bhattacharya et al., 1996, *Water Res.* 30, 2239-2246; Mirzoyan et al., 2008, *Aquaculture,* 279, 35-41; Tal, *Aquaculture* 286, 28-35). COD:SO$_4$ ratios greater than 1.7-2.7 favor methanogens over sulfate reducing bacteria (Bitton, 2005, Wastewater Microbiology, 3d Ed., Wiley-Lizz Inc., New York, pp. 345-370). The COD:SO$_4$ ratio of the seawater used in this study was 21:1, which already favored methanogenesis and increasing the ratio by eliminating the sulfate did not further stimulate and even inhibited slightly bioconversion of fish waste to methane. A COD:SO$_4$ ratio that exceeds 10 is typical of marine/brackish RAS concentrated wastes (Bhattacharya et al., 1996, *Water Res.* 30, 2239-2246; Mirzoyan et al., 2008, *Aquaculture* 279, 35-41). The results indicate that both fish waste and undigested fish meal likely provide a rich medium and essential growth factors were not limiting the rates and extent of biomethane production.

Municipal systems typically operate between 25 and 40° C. with maximum activity at 35° C. (Bitton, 2005, Wastewater Microbiology, 3d Ed., Wiley-Lizz Inc., New York, pp. 345-370). As expected, increasing the temperature of the fish sludge digesting consortium did have a positive effect on the amount of methane produced by the enriched consortium. However, an increase in temperature from 26 to 35° C. only increased the methane yield by 11.8% with no apparent decrease in rate. The increase in methane production is not enough to offset the cost of having to increase the temperature of a commercial system by 10° C. At 20° C. there was a significant reduction in the rate of methane production. The results indicate that an RAS bioreactor can be operated optimally at temperatures from 26 to 35° C. with minimal changes in the hydraulic retention time.

A COD:N ratio of approximately 50-70:1 has been reported as optimal for stable performance of methanogenic digestion (Alvarez et al., 2010), but in the current study over 90% of theoretical total methane was produced at a COD:N ratio 15:1. Mshandete et al (Mshandete et al., 2004, *Bioresour. Technol.* 95, 19-24) reported an increase in methane yield by increasing the COD:N ration of fish waste with sisal pulp. However, attempts to improve the efficiency further in the current study by increasing the COD over half to 39:1 with a soluble carbon source increased the amount of total gas produced but decreased slightly the amount of methane kg$_{COD}^{-1}$. The results indicate that the methanogenic consortium was adapted to a low COD:N ratio characteristic of proteinaceous fish waste.

There was a transition of the predominant species as inoculum originating from the RAS solid waste settling tank was sequentially transferred with marine fish waste under an anaerobic headspace. The predominant fermentative phylotypes in the initial methanogenic enrichment had highest sequence identity to species of *Bacteriodales*, which commonly originate from the feces of humans and other species with high protein diets including fish (Cahill, 1990, *Microb. Ecol.* 19, 21-41; Kabiri et al., 2010, Assessment of Human Microbial Pollution of Surface Waters by Microbial Source Tracking Water & Environmental Technology Center; Wu et al., 2011, *Science* 334, 105-108), and *Clostridiales* that include species of protein fermenting acetogens (Pikuta et al., *Extremophiles,* 7, 327-334). Archaeal phylotypes closely related to hydrogen utilizing *Methanogenium* spp. and acetate utilizing *Methanosarcina* spp. were also detected. As the efficiency of methanogenesis achieved a steady state rate beyond the seventh sequential transfer the composition of the consortium changed, although several microorganisms were maintained throughout the enrichment process.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method for conversion of marine fish waste to biomethane, comprising exposing the marine fish waste to a methanogenic microbial consortium comprising
   (a) an isolated *Dethiosulfovibrio* sp. microorganism comprising the 16S ribosomal subunit nucleotide sequence of SEQ ID NO: 1;
   (b) an isolated *Fusobacteriacea* microorganism comprising the 16S ribosomal subunit nucleotide sequence of SEQ ID NO: 2;
   (c) an isolated *Methanogenium* sp. microorganism comprising the 16S ribosomal subunit nucleotide sequence of SEQ ID NO: 3;
   (d) an isolated *Methanoplanus* sp. microorganism comprising the 16S ribosomal subunit nucleotide sequence of SEQ ID NO: 4;
   (e) an isolated *Methanosarcina* sp. microorganism comprising the 16S ribosomal subunit nucleotide sequence of SEQ ID NO: 5,
under anaerobic conditions effective for microbial action on the marine fish waste to produce biomethane.

2. The method of claim 1, wherein the marine fish waste are exposed to the methanogenic microbial consortium in a methanogenic bioreactor.

3. The method of claim 2, wherein the methanogenic bioreactor is a modified upflow anaerobic sludge blanket reactor.

4. The method of claim 2, wherein the temperature in the methanogenic bioreactor is between about 26 and 35° C.

5. The method of claim 1, wherein the marine fish waste is not pretreated.

6. The method of claim 4, wherein the conversion rate is greater than about 90%.

7. A closed, recirculating marine aquaculture system comprising brackish or salt water comprising marine fish waste, a tank comprising a marine species, and a methanogenic bioreactor comprising a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5.

8. The method of claim 7, wherein the methanogenic bioreactor is a modified upflow anaerobic sludge blanket reactor.

9. The method of claim 7, wherein the temperature in the methanogenic bioreactor is between about 26 and 35° C.

10. The method of claim 7, wherein the marine fish waste is not pretreated.

11. The method of claim 9, wherein the conversion rate is greater than about 90%.

12. The method of claim 7, wherein the marine aquaculture system comprises brackish water.

13. The method of claim 7, wherein the marine aquaculture system comprises salt water.

14. A methanogenic microbial consortium for conversion of marine fish waste to biomethane, the consortium comprising:
   (a) an isolated *Dethiosulfovibrio* sp. microorganism comprising the 16S ribosomal subunit nucleotide sequence of SEQ ID NO: 1;
   (b) an isolated *Fusobacteriacea* microorganism comprising the 16S ribosomal subunit nucleotide sequence of SEQ ID NO: 2;
   (c) an isolated *Methanogenium* sp. microorganism comprising the 16S ribosomal subunit nucleotide sequence of SEQ ID NO: 3;
   (d) an isolated *Methanoplanus* sp. microorganism comprising the 16S ribosomal subunit nucleotide sequence of SEQ ID NO: 4; and
   (e) an isolated *Methanosarcina* sp. microorganism comprising the 16S ribosomal subunit nucleotide sequence of SEQ ID NO: 5.

15. The methanogenic microbial consortium of claim 14, wherein a stable ratio of members (a)-(e) of the consortium is maintained through sequential transfers.

16. The methanogenic microbial consortium of claim 14, wherein (a)-(e) are the only methanogenic microorganisms in the methanogenic microbial consortium.

17. A biomethane production apparatus, comprising a bioreactor containing a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5.

18. The biomethane production apparatus of claim 17, wherein the bioreactor is methanogenic bioreactor comprising a modified upflow anaerobic sludge blanket reactor.

19. A method of producing biomethane, said method comprising exposing a methanogenic substrate to a methanogenic microbial consortium comprising (a) an isolated *Dethiosulfovibrio* sp. microorganism comprising the 16S ribosomal subunit nucleotide sequence of SEQ ID NO: 1; (b) an isolated *Fusobacteriacea* microorganism comprising the 16S ribosomal subunit nucleotide sequence of SEQ ID NO: 2; (c) an isolated *Methanogenium* sp. microorganism comprising the 16S ribosomal subunit nucleotide sequence of SEQ ID NO: 3; (d) an isolated *Methanoplanus* sp. microorganism comprising the 16S ribosomal subunit nucleotide sequence of SEQ ID NO: 4; and (e) an isolated *Methanosarcina* sp. microorganism comprising the 16S ribosomal subunit nucleotide sequence of SEQ ID NO: 5 under conditions effective to microbially generate biomethane, and separating the generated biomethane from the microbial consortium to recover a biomethane product.

20. The method of claim 19, wherein the methanogenic substrate is marine fish waste.

* * * * *

UNITED STATES PATENT AND TRADEMARK OFFICE
CERTIFICATE OF CORRECTION

PATENT NO. : 10,400,255 B2
APPLICATION NO. : 15/378480
DATED : September 3, 2019
INVENTOR(S) : Kevin R. Sowers It is certified that error appears in the above-identified patent and that said Letters Patent is hereby corrected as shown below:

On the Title Page

Page 2, item [56], Column 2 Line 48, following the heading "Other Publications" in the right column of the listing of references, the pages "pp 491-491" listed for the last reference Zhao, J. S., et al. should read -- pp 491-497 --.

Signed and Sealed this
Fifteenth Day of October, 2019

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 1419
<212> TYPE: DNA
<213> ORGANISM: Dethiosulfovibrio sp. F2

<400> SEQUENCE: 1
tgcaagtggg acgaaggtat atatttgaag gcttcggctg gacgatatat atactgagtc      60
gcggacgggt gagtaatgcg tgaggacctg tccatcagag ggggatagcc ccgggaaacc     120
gggattaaaa ccccataagc ccaagggtga aagggagcaa tccgctgatg gagggtctcg     180
cgtcctatca ggtagttggt ggggtaaagg cctaccaagc cgaagacggg tagccggact     240
gagaggttga ccggccacat tggaactgag atacggtcca gactcctacg ggaggcagca     300
gtggggaata ttgggcaatg ggcggaagcc tgacccagcg acgccgcgtg agggaagacg     360
gtcttcggat tgtaaacctc tgttgcaggg gaagaaggaa gtgacggtac cctgcgagga     420
agccccggca aactacgtgc cagcagccgc ggtaacacgt aggggcgag cgttgtccgg     480 aattactggg cgtaaagggc gcgtaggctg cgaggcaagt cgggtgtaaa aggcacgggc     540
tcaacccgtg tatgcactcg aaactgtctt gctggagggg tagagaggca agcggaattc     600
```

```
ccggtgtagc ggtgaaatgc gtagatatcg ggaagaacac cagtggcgaa ggcggcttgc    660
tggctacacc ctgacgctga ggcgcgaaag ccaggggagc gaaccggatt agatacccgg    720
gtagtcctgg cagtaaacga tgaatgctag gtgtgggtgg gtcaaaccat ccgtgccgca    780
gttaacgcga taagcattcc gcctggggag tacggccgca aggttgaaac tcaaaggaat    840 tgacggggc ccgcacaagc ggtggagcac gtggtttaat tcgatgcaaa ccgaagaacc    900
ttacctgggc ttgacatcta ggtggtattg acctgaaagg tgatagacca tattttcgga    960
tatggagcct agacaggtgc tgcatggctg tcgtcagctc gtgtcgtgag atgttgggtt   1020
aagtcccgca acgagcgcaa ccctattgt cagttgctaa cgtttaaggc gagcactctg   1080
gcgagactgc cggcgacaag ccggaggaag gtggggacga cgtcaagtca tcatggccct   1140
tatgtccagg gcaacacaca tgctacaatg gccgatacag agggaagcga aggcgcgagt   1200
tggagcggat cccaaaaagt cggtcccagt tcggattgca gtctgcaact cgactgcatg   1260
aagttggaat cgctagtaat cgcaaatcag ctaagttgcg gtgaatacgt tcccgggcct   1320
tgtacacacc gcccgtcaca ccatccgagt tgggtgcacc cgaagccgga ggctgaaccc   1380
ttaggggaca gatccgtcga aggtgtgtct ggtaaggag                          1419

<210> SEQ ID NO 2
<211> LENGTH: 1507
<212> TYPE: DNA
<213> ORGANISM: Fusobacteriaceae sp. F3

<400> SEQUENCE: 2
agagtttgat cctggctcag gatgaacgct gacagaatgc ttaacacatg caagtctact     60
tgaattcact tcggtgatag taaggtggcg gacgggtgag taacacgtaa agaacttgcc    120
ttacagtctg ggacaactat tggaaacgat agctaatacc ggatattatg attttctcgc    180
atgggaaagt tatgaaagct atatgcgctg taagagagct ttgcgtccca ttagctagtt    240
ggtgaggtaa cggctcacaa aggcgacgat gggtagccgg cctgagaggg tgaacggcca    300
caaggggact gagacacggc ccttactcct acgggaggca gcagtgggga atattggaca    360
atggaccaaa agtctgatcc agcaattctg tgtgcacgat gacggtcttc ggattgtaaa    420
gtgctttcag ttgggaagaa aaaaatgacg gtaccaacag aagaagcgac ggctaaatac    480
gtgccagcag ccgcggtaat acgtatgtcg caagcgttat ccggatttat gggcgtaaa    540 gcgcgtctag gtggtttgat aagtctgatg tgaaaatgcg gggctcaact ccgtattgcg    600
ttggaaactg tcaaactaga gtatcggaga ggtgggcgga actacaagtg tagaggtgaa    660
attcgtagat atttgtagga atgccgatag agaagtcagc tcactggacg aatactgaca    720
ctgaagcgcg aaagcatggg gagcaaacag gattagatac cctggtagtc catgccgtaa    780
acgatgatta ctaagcgtcg ggggtcgaac ctcggcactc aagctaacgc gataagtaat    840
ccgcctgggg agtacgtacg caagtatgaa actcaaagga attgacgggg acccgcacaa    900
gtggtggagc atgtggttta attcgacgca acgcgaggaa ccttaccagc gtttgacatc    960
ctaagaatga aaagagatt tttcagtgct ccttcgggag aacttagaga caggtggtgc   1020
atggctgtcg tcagctcgtg tcgtgagatg ttgggttaag tcccgcaacg agcgcaaccc   1080
ctattgtatg ttgccatcat taagttgggc actcatgcga tactgcctgc gacgagcagg   1140
aggaaggtgg ggatgacgtc aagtcatcat gccccttata cgctgggcta cacacgtgct   1200
acaatgggca gtacagagag aagccatccc gcgaggggga gcaaatctca gaaagctgtt   1260
```

```
cgtagttcgg attgtactct gcaactcgag tacatgaagt tggaatcact agtaatcgca    1320
gatcagcaat gctgcggtga atacgttctc gggtcttgta cacaccgccc gtcacaccac    1380
gagagttggt tgcacctgaa gtagcaggcc taaccgtaag gaaggatgct ccgagggtgt    1440
ggttagcgat tggggtgaag tcgtaacaag gtatccgtac gggaacgtgc ggctggatca    1500
cctcctt                                                               1507

<210> SEQ ID NO 3
<211> LENGTH: 1410
<212> TYPE: DNA
<213> ORGANISM: Methanogenium sp. M3

<400> SEQUENCE: 3
tctgccagag gtcactgcta tcggggttcg attaagccat gcgagttgag agggtttaga     60
ccctcagcgg actgctcagt aacacgtgga taacctggcc taaggtggag ataaccccg    120 ggaaactggg gataatactc catagattag agatactgga atgttcttta gtcgaaagtt    180
ccggcgcctt agggtggatc tgcggtcgat taggttgttg ttggggtaac ggcccaacaa    240
gcctgtaatc gatacgggtt gtgggagcaa gagcccggag atggaatctg agacacgatt    300
ccaggcccta cggggcgcag caggcgcgaa aactttacaa tgcaggaaac tgtgataagg    360
gaaccccgag tgcccgtata cgcgggctgt ccaggtgttt aaaacgcatc tgaagaaagg    420
gccgggcaag accggtgcca gccgccgcgg taataccggc ggctcgagtg gtggccacta    480
ttattgggct aaagcgtccg tagctggacg cgataagtct cttgggaaat ccgccggctt    540
aaccggcggg cgtccagggg atactgttgg tctaggaccc gggagaggtg agaggtactc    600 cggggtagg agtgaaatcc tgtaatccct gggggaccac cgatggcgaa ggcatctcac    660
cagaacggct ccgacagtga gggacgaaag ctgggggagc gaaccggatt agatacccgg    720
gtagtcccag ccgtaaacta tgcacgttag gtgtaccggt gaccacgagt cactggggtg    780
ccgaagggaa accgtgaaac gtgccgcctg gaagtacggt cgcaaggct gaaacttaaa    840 ggaattggcg ggggagcacc acaacggtg gagcctgcgg tttaattgga ctcaacgccg    900
gaaatctcac cggataagac agcggaatga taaccgggct gaagactctg tttgaccagc    960
tgagaggagg tgcatggccg tcgtcagttc gtactgtgaa gcatcctgtt aagtcaggca    1020
acgagcgaga cccacgccaa cagttgctag cttgttctcc ggaatgaaga ggacactgtt    1080
gggaccgcct ctgctaaaga ggaggaagga atgggcaacg gtaggtcagc atgccccgaa    1140
ttatccgggc tacacgcggg ctacaatggg caggacaatg ggatcgaca ccgaaaggtg    1200 aaggcaatct cttaaacctg tcctaagttc ggattgtggg ctgtaactcg cccacatgaa    1260
gctggaatcc gtagtaatcg cgtttcaaca tagcgcggtg aatgcgtccc tgctccttgc    1320
acacaccgcc cgtcaaacca tccgagtgag gtctggatga gcctgtggtt tttgccgcag    1380
tcgaatctag gttttgcaag gagggttaag                                     1410

<210> SEQ ID NO 4
<211> LENGTH: 1355
<212> TYPE: DNA
<213> ORGANISM: Methanoplanus sp. M7

<400> SEQUENCE: 4
atgcgagtcg agagggttca gacccctcggc ggactgctca gtaacacgtg gataacctgc     60
cctaaggtga agcataaccc cgggaaactg gggataatac tccataggtt agagatactg    120
gaatgttctt taatcgaaag ttccggcgcc ttaggatgga tctgcggccg attaggtagt    180
```

```
tgttggggta acggcccaac aagcctgtaa tcggtacggg ttgtgggagc aagagcccgg      240
agatggaatc tgagacacga ttccaggccc tacgggcgc agcaggcgcg aaaactttac      300
aatgcaggaa actgtgataa gggaaccccg agtgcccgta tacgcgggct gtccgggtgt      360
ataaaaagca tctgaagaaa gggccgggca agaccggtgc cagccgccgc ggtaataccg      420
gcggctcgag tggtgaccac ttttattggg cttaaagcgt tcgtagctgg actcttaagt      480
ctcttgggaa atcccgcggc tcaaccgtgg gcgtttaag agatactggg agtctaggaa      540
ccgggagagg taagaggtac ttcggggta gaagtgaaat tctgtaatcc tcgagggacc      600
accgatggcg aaggcatctt accagaacgg cttcgacagt gaggaacgaa agctgggga      660 gcgaacggga ttagataccc cggtagtccc agccgtaaac gatgcgcgtt aggtgtactg      720
gtgaccacga gtcactgggg tgccgaaggg aaaccgtgaa acgtgccgcc tgggaagtac      780
ggtcgcaagg ctgaaactta aaggaattgg cggggagca ccacaacggg tggagcctgc      840
ggtttaattg gactcaacgc cggaaatctc accggataag acagcggaat gatagcctgg      900
ctgaagacct tgcttgacca gctgagagga ggtgcatggc cgtcgtcagt tcgtactgtg      960
aagcatcctg tttagtcagg caacgagcga gacccacgcc aacagttgcc agcatgttct     1020
ccggaatgat ggggacactg ttgggaccgc ctctgctaaa gaggaggaag gaatgggcaa     1080
cggtaggtca gcatgccccg aattatccgg gctacacgcg ggctacaatg gtcaggacaa     1140
tgagaaacgg cactgaaaag tgtagttaat ctcctaaacc tgtcccaagt tcggattgtg     1200
ggctgcaact cgcccacatg aagctggaat ccgtagtaat cgcgcttcaa acagcgcgg     1260 tgaataagtc cctgctcctt gcacacaccg cccgtcaaac catcttagtg aggtttggat     1320
gaggctgtag ttattgctac agtcgaatct aggtt                                1355
```

<210> SEQ ID NO 5
<211> LENGTH: 1363
<212> TYPE: DNA
<213> ORGANISM: Methanosarcina sp. M15

<400> SEQUENCE: 5

```
gtgaacatgg cgtactgctc agtaacacgt ggataacctg cccttgggtc cggcataacc      60
ccgggaaact ggggataatt ccggataccg catatctgct ggaatgcttt atgcgtcaaa     120
tggattcgtc tgcccaagga tggatctgcg gcctatcagg tagtagtggg tgtaatgtac     180
ctactagcca acgacgggta cgggttgtga gagcaagagc ccggagatgg attctgagac     240
atgaatccag gccctacggg gcgcagcagg cgcgaaaact ttacaatgcg ggaaaccgtg     300 ataagggac accgagtgcc agcatcatat gctggctgtc cgggtgttta aactacacct     360
gttagcaagg gccgggcaag accggtgcca gccgccgcgg taacaccggc ggcccgagtg     420
gtgatcgtga ttattgggtc taaagggtcc gtagccggtt tggtcagtcc tccgggaaat     480
ctgatagctt aactattagg ctttcggggg atactgccag gcttggaacc gggagaggta     540
agaggtacta caggggtagg agtgaaatct tgtaatccct gtgggaccac ctgtggcgaa     600
ggcgtcttac cagaacgggt tcgacggtga gggacgaaag ctgggggcac gaaccggatt     660 agataccccgg gtagtcccag ccgtaaacga tgctcgctag gtgtcaggca tggcgcgacc     720
gtgtctggtg ccgcagggaa gccgtgaagc gagccacctg gaagtacgg ccgcaaggct     780 gaaacttaaa ggaattggcg ggggagcaca acaacgggtg gagcctgcgg tttaattgga     840
ctcaacgccg gacaactcac cggggggcgac agcaatatgt aggccaagct gaagactttg     900
```

```
cctgaatcgc tgagaggagg tgcatggccg tcgccagttc gtactgtgaa gcatcctgtt        960
aagtcaggca acgagcgaga cccgtgccca ctgttaccag catgtcctcc gggacgatgg       1020
gtactctgtg gggaccgccg gtgttaaatc ggaggaaggt gcgggccacg gtaggtcagt       1080
atgccccgaa tctcccggge tacacgcggg ctacaatgga tgggacaatg ggtccctccc       1140
ccgaaagggg ctggtaatct cacaaaccca tccgtagttc ggatcgaggg ctgtaactcg       1200
ccctcgtgaa gctggaatcc gtagtaatcg cgtttcaata tagcgcggtg aatacgtccc       1260
tgctccttgc acacaccgcc cgtcaaacca cccgagtgag gtatgggtga gggcacggac       1320
tctgtgccgt gttcgaacct gaattttgca aggggggtta agt                         1363
```